(12) United States Patent
Ohrui et al.

(10) Patent No.: US 11,964,930 B2
(45) Date of Patent: Apr. 23, 2024

(54) ORGANIC COMPOUND AND ORGANIC LIGHT-EMITTING ELEMENT

(71) Applicant: CANON KABUSHIKI KAISHA, Tokyo (JP)

(72) Inventors: Hiroki Ohrui, Kawasaki (JP); Hirokazu Miyashita, Ebina (JP); Satoru Shiobara, Hiratsuka (JP); Yosuke Nishide, Kawasaki (JP); Naoki Yamada, Inagi (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 753 days.

(21) Appl. No.: 17/010,293

(22) Filed: Sep. 2, 2020

(65) Prior Publication Data

US 2021/0139417 A1    May 13, 2021

(30) Foreign Application Priority Data

Nov. 7, 2019    (JP) .................................. 2019-202381

(51) Int. Cl.
*C07C 255/49*    (2006.01)
*C07C 255/51*    (2006.01)
(Continued)

(52) U.S. Cl.
CPC .......... *C07C 255/51* (2013.01); *C07C 255/49* (2013.01); *H10K 85/624* (2023.02); *H10K 50/13* (2023.02)

(58) Field of Classification Search
CPC ... C07C 255/49; C07C 255/50; C07C 255/51; C07C 2603/26
See application file for complete search history.

(56) References Cited

U.S. PATENT DOCUMENTS 8,293,384 B2 * 10/2012 Kamatani ............ C07D 213/06
585/27
8,940,413 B2 *  1/2015 Kamatani ............ C07C 49/792
585/27
(Continued)

FOREIGN PATENT DOCUMENTS

CN        102245546 A    11/2011
CN        112441949 A     3/2021
(Continued)

OTHER PUBLICATIONS

Wu, Tsun-Cheng et al., "Synthesis and Structural Analysis of a Highly Curved Buckybowl Containing Corannulene and Sumanene Fragments", Journal of the American Chemical Society, 2011, pp. 16319-16321, vol. 133, No. 41.

(Continued)

*Primary Examiner* — Amanda C. Walke
(74) *Attorney, Agent, or Firm* — CANON U.S.A., INC. IP Division

(57) ABSTRACT

An organic compound represented by formula [1].

(Continued)

-continued

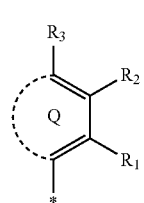

[1-1]

In the formula rings Q represented by formula [1-1] are each independently present at positions *1 and *2 such that positions * of the rings Q correspond to the positions *1 and *2. The rings Q may be the same or different. $R_4$ and $R_5$ represent groups each independently selected from the group consisting of a hydrogen atom and a substituted or unsubstituted aryl group. The rings Q are aromatic hydrocarbons. $R_1$ to $R_3$ represent groups each independently selected from the group consisting of a hydrogen atom, a substituted or unsubstituted alkyl group, a substituted or unsubstituted aryl group, and a cyano group. At least one of $R_1$ to $R_3$ represents a cyano group.

20 Claims, 6 Drawing Sheets

(51) Int. Cl.
*H10K 85/60* (2023.01)
*H10K 50/13* (2023.01)

(56) References Cited

U.S. PATENT DOCUMENTS

| | | | | |
|---|---|---|---|---|
| 9,472,766 | B2* | 10/2016 | Itabashi | C07D 235/18 |
| 9,705,089 | B2* | 7/2017 | Nishide | H10K 85/624 |
| 9,818,957 | B2* | 11/2017 | Nishide | H10K 85/621 |
| 10,032,987 | B2* | 7/2018 | Ishii | H10K 85/626 |
| 10,937,979 | B2* | 3/2021 | Yamada | H10K 85/633 |
| 11,271,164 | B2* | 3/2022 | Saito | C07C 13/62 |
| 2010/0026171 | A1 | 2/2010 | Negishi | |
| 2013/0033416 | A1 | 2/2013 | Kamatani | |
| 2019/0013476 | A1* | 1/2019 | Saito | H10K 85/624 |

FOREIGN PATENT DOCUMENTS

| | | |
|---|---|---|
| DE | 10 2019 108200 A1 | 10/2019 |
| EP | 2314558 B1 | 5/2014 |
| EP | 2379473 B1 | 2/2017 |
| JP | 2009-221180 A | 10/2009 |
| JP | 2010-143879 A | 7/2010 |
| JP | 2010-254610 A | 11/2010 |
| JP | 2012-246258 A | 12/2012 |
| JP | 2016-015388 A | 1/2016 |
| JP | 2018-76259 A | 5/2018 |
| JP | 2020-026406 A | 2/2020 |
| JP | 2021-038187 A | 3/2021 |
| WO | 2007/099802 A | 9/2007 |
| WO | 2008/120806 A1 | 10/2008 |
| WO | 2010/071224 A1 | 6/2010 |
| WO | 2013/042357 A1 | 3/2013 |
| WO | 2018/179482 A1 | 10/2018 |
| WO | 2021/085131 A1 | 5/2021 |

OTHER PUBLICATIONS

Wu, Tsun-Cheng et al., "Bowl-Shaped Fragments of C70 or Higher Fullerenes: Synthesis, Structural Analysis, and Inversion Dynamics", Angewandte Chemie, International Edition, 2013, pp. 1289-1293, vol. 52, No. 4.

Schmidt, Bernd M. et al., "Fluorinated and Trifluoromethylated Corannulenes", Chemistry—A European Journal, 2013, pp. 13872-13880, vol. 19, No. 41.

* cited by examiner

ORGANIC COMPOUND AND ORGANIC LIGHT-EMITTING ELEMENT

BACKGROUND OF THE INVENTION

Field of the Invention

The present disclosure relates to an organic compound and an organic light-emitting element including the organic compound.

Description of the Related Art

Organic light-emitting elements (also referred to as organic electroluminescent elements or organic EL elements) are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state. Recent remarkable progress in organic light-emitting elements can achieve low driving voltage, various emission wavelengths, high-speed response, and reductions in the thickness and weight of light-emitting devices.

Luminescent organic compounds have been enthusiastically created to date. This is because it is important to create compounds having good light-emitting properties in order to provide high-performance organic light-emitting elements. Japanese Patent Laid-Open Nos. 2010-254610, 2012-246258, and 2018-76259 respectively disclose a compound 1-A, a compound 1-B, and a compound 1-C below each having an acenaphtho[1,2-k]benzo[e]acenaphthophenanthrene skeleton as a basic skeleton.

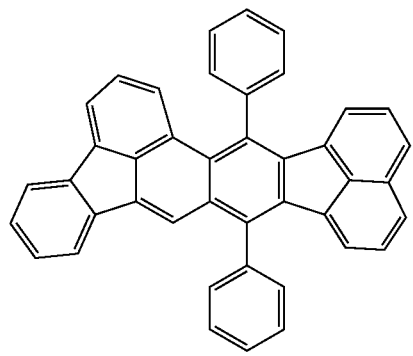

1-A

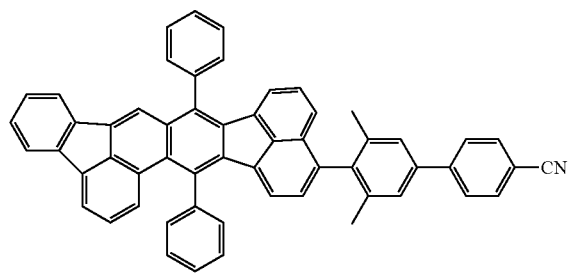

1-B

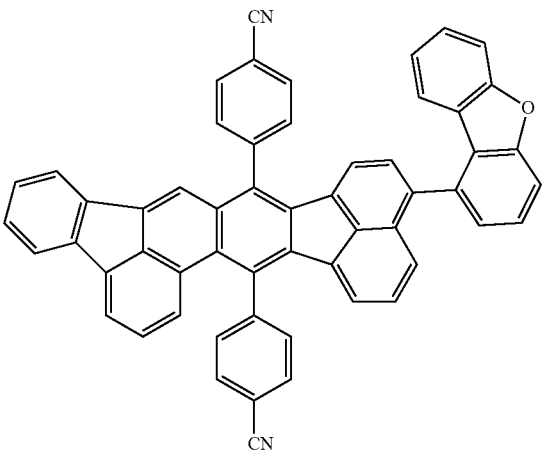

1-C

As a result of studies conducted by the present inventors, the compounds 1-A to 1-C contribute to emitting blue light.

The compound 1-A is a blue light-emitting material with a high color purity, but is desired to have further improved electron acceptability. On the other hand, the compounds 1-B and 1-C are blue light-emitting materials having high electron acceptability, but are desired to have a further improved color purity of blue light emission. Organic light-emitting elements including such a compound are desired to have further improved color purity or durability.

SUMMARY OF THE INVENTION

In view of the foregoing, the present disclosure provides a blue light-emitting material having a high reduction potential, high electron acceptability, and a high color purity. The present disclosure also provides an organic light-emitting element having a high color purity and high driving durability.

An organic compound according to the present disclosure is represented by formula [1] below.

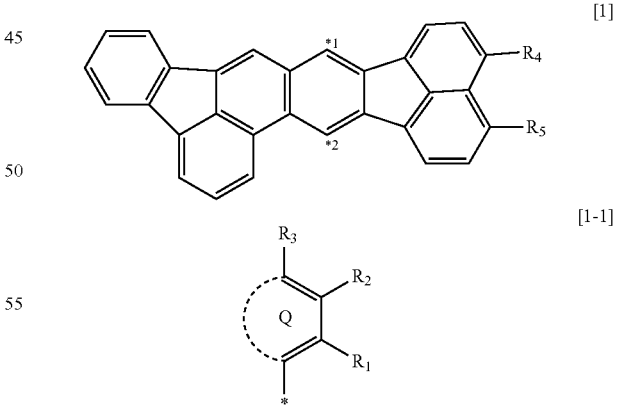

In the formula [1], rings Q represented by formula [1-1] are each independently present at positions *1 and *2 such that positions * of the rings Q correspond to the positions *1 and *2. The rings Q may be the same or different.

$R_4$ and $R_5$ represent groups each independently selected from the group consisting of a hydrogen atom and a substituted or unsubstituted aryl group.

The rings Q are aromatic hydrocarbons. $R_1$ to $R_3$ represent groups each independently selected from the group consisting of a hydrogen atom, a substituted or unsubstituted alkyl group, a substituted or unsubstituted aryl group, and a cyano group. At least one of $R_1$ to $R_3$ represents a cyano group.

Further features of the present disclosure will become apparent from the following description of exemplary embodiments with reference to the attached drawings.

DESCRIPTION OF THE EMBODIMENTS

Organic Compound

Figure 1A:
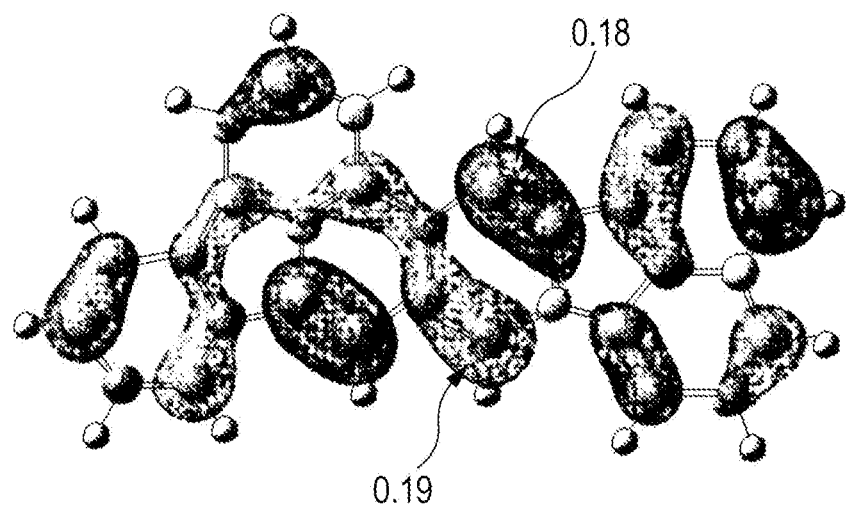
FIGS. 1A and 1B illustrate the electron orbital distributions of HOMO and LUMO of an acenaphtho[1,2-k]benzo[e]acenaphthophenanthrene skeleton.

First, an organic compound according to this embodiment will be described. The organic compound according to this embodiment is represented by formula [1] below.

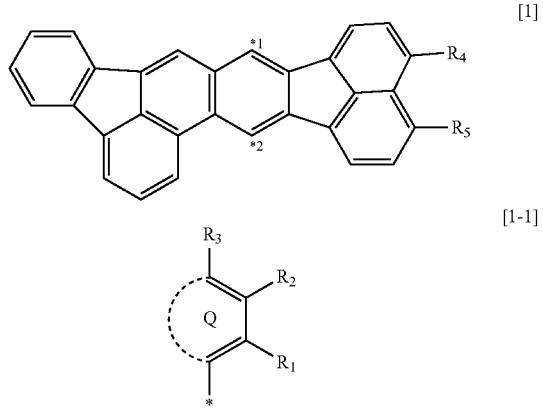

In the formula [1], rings Q represented by formula [1-1] are each independently present at positions *1 and *2 such that positions * of the rings Q correspond to the positions *1 and *2. The two rings Q may be the same or different.

$R_4$ and $R_5$ represent groups each independently selected from the group consisting of a hydrogen atom and a substituted or unsubstituted aryl group.

Non-limiting examples of the aryl group represented by $R_4$ and $R_5$ include a phenyl group, a naphthyl group, an indenyl group, a biphenyl group, a terphenyl group, and a fluorenyl group. Among them, an aryl group having 6 to 18 carbon atoms is preferably used, and a phenyl group, a naphthyl group, a fluorenyl group, and a phenanthrenyl group are more preferably used.

Non-limiting examples of the substituent that may be further introduced to the aryl group represented by $R_4$ and $R_5$ include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heteroaryl groups such as a pyridyl group and a pyrrolyl group; halogen atoms such as fluorine, chlorine, bromine, and iodine; and cyano groups.

At least one of $R_4$ and $R_5$ may represent a hydrogen atom. Preferably, one of $R_4$ and $R_5$ represents a hydrogen atom and the other represents a substituted or unsubstituted aryl group. More preferably, the other represents a group selected from the group consisting of a substituted or unsubstituted phenyl group, a substituted or unsubstituted naphthyl group, a substituted or unsubstituted fluorenyl group, and a substituted or unsubstituted phenanthrenyl group.

The ring Q is an aromatic hydrocarbon and may be an aromatic hydrocarbon having 6 to 18 carbon atoms. Non-limiting examples of the aromatic hydrocarbon represented by the ring Q include benzene, naphthalene, phenanthrene, fluorene, fluoranthene, pyrene, anthracene, and triphenylene. From the viewpoint of sublimability, benzene and naphthalene, which have a low molecular weight, can be particularly used.

$R_1$ to $R_3$ represent groups each independently selected from the group consisting of a hydrogen atom, a substituted or unsubstituted alkyl group, a substituted or unsubstituted aryl group, and a cyano group. At least one of $R_1$ to $R_3$ represents a cyano group.

Non-limiting examples of the alkyl group represented by $R_1$ to $R_3$ include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group.

Non-limiting examples of the aryl group represented by $R_1$ to $R_3$ include a phenyl group, a naphthyl group, an indenyl group, a biphenyl group, a terphenyl group, and a fluorenyl group.

Non-limiting examples of the substituent that may be further introduced to the alkyl group and the aryl group represented by $R_1$ to $R_3$ include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heteroaryl groups such as a pyridyl group and a pyrrolyl group; halogen atoms such as fluorine, chlorine, bromine, and iodine; and cyano groups.

The organic compound according to this embodiment may be an organic compound represented by formula [2] below.

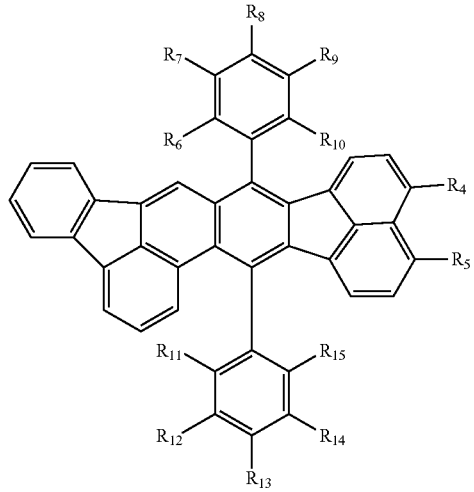

[2]

$R_6$ to $R_{15}$ represent groups each independently selected from the group consisting of a hydrogen atom, a substituted or unsubstituted alkyl group, a substituted or unsubstituted aryl group, and a cyano group. At least one of $R_6$ to $R_{15}$ represents a cyano group. The alkyl group and aryl group represented by $R_6$ to $R_{15}$ and the substituent that may be introduced to the alkyl group and the aryl group are the same as those described for $R_1$ to $R_3$.

At least two of $R_7$ to $R_9$ may represent a cyano group, and at least two of $R_{12}$ to $R_{14}$ may represent a cyano group. $R_7$ or $R_9$ may represent a cyano group, and Ria or $R_{14}$ may represent a cyano group.

Next, a method for synthesizing the organic compound according to this embodiment will be described. The organic compound according to this embodiment is synthesized through, for example, the following reaction scheme (synthesis route 1).

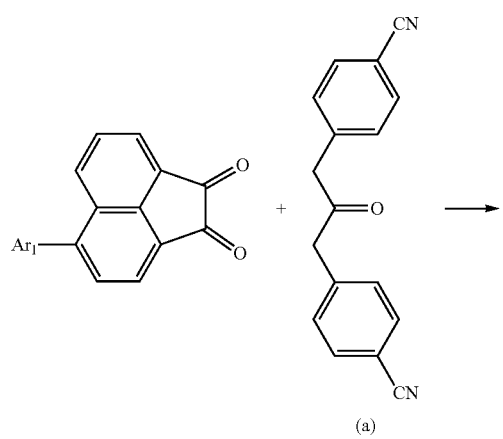

(a)

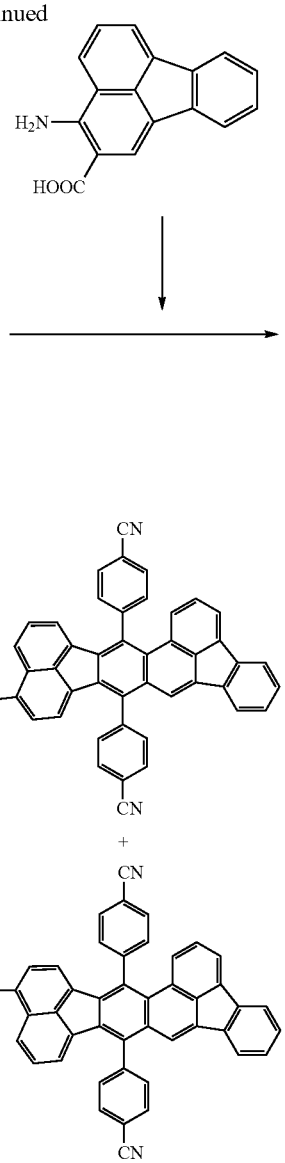

Herein, various compounds can be obtained by appropriately changing the compound (a) and the substituent Ari. The details of the synthesis method will be described in Examples.

Since the organic compound according to this embodiment has the following features (1) and (2) and may have the following features (1) to (3), the organic compound is a chemically stable compound that contributes to emitting blue light with a high color purity and has a high reduction potential. By using this organic compound, an organic light-emitting element having a high color purity and high durability can also be provided.

The "basic skeleton" herein refers to a skeleton in which hydrogen atoms are present at positions *1 and *2 in the formula [1] instead of the rings Q and $R_4$ and $R_5$ represent a hydrogen atom.

(1) The basic skeleton is a skeleton that has an emission wavelength in a blue region with a high color purity and has electron acceptability.

(2) The ring Q has an electron-withdrawing cyano group and bonds to the basic skeleton at a position at which the electron orbital distribution of LUMO of the basic skeleton is relatively lower than that of HOMO.

(3) R₄ and R₅ represent groups having no lone pair.

Hereafter, these features will be described.

(1) The basic skeleton is a skeleton that has an emission wavelength in a blue region with a high color purity and has electron acceptability.

When the organic compound represented by the formula [1] is made, the present inventors have focused on the basic skeleton itself.

To emit blue light with a high color purity, the basic skeleton itself needs to be in a blue region with a high color purity. In this embodiment, the desired emission wavelength region is a blue region with a high color purity, which is specifically a region in which the maximum emission wavelength in a dilute solution is 430 nm or more and 450 nm or less.

On the other hand, organic light-emitting materials need to have high charge stability. To achieve this, high electron acceptability is required. In organic light-emitting elements, carrier recombination caused when an organic compound sandwiched between electrodes is repeatedly oxidized and reduced between its molecules allows the organic compound to have an excited state and a ground state in a repeated manner Consequently, the organic light-emitting elements emit light. Therefore, the compound that is unstable in terms of charge transfer is chemically changed to a different compound through an oxidation-reduction process and in an excited state. This impairs the intrinsic element characteristics, which decreases the luminance of the organic light-emitting element and deteriorates the durability of the element during continuous driving. To suppress such deterioration, charge stability is required and thus high electron acceptability is required. High reduction potential is exemplified as one of design strategies for materials having high electron acceptability.

Herein, the organic compound according to this embodiment is a compound having, as a basic skeleton, an acenaphtho[1,2-k]benzo[e]acenaphthophenanthrene skeleton obtained by condensing two fluoranthene skeletons. Fluoranthene is an aromatic hydrocarbon having a five-membered ring. The feature of the aromatic hydrocarbon having a five-membered ring is as follows. Such an aromatic hydrocarbon has a 5π electron system. If the aromatic hydrocarbon accepts one electron (is reduced), the aromatic hydrocarbon has a 6π electron system, which causes aromatic stabilization in accordance with the Hückel's rule. Therefore, fluoranthene has higher electron acceptability and more stable for charge transfer than aromatic hydrocarbons (e.g., anthracene and pyrene) constituted by only a six-membered ring.

To describe the properties of the basic skeleton of the organic compound according to this embodiment, the following comparative compound R₁ and the comparative compound 1-A have been compared with each other in terms of maximum emission wavelength and reduction potential. The comparative compound R₁ is a compound obtained by introducing a phenyl group to 7 and 12 positions of benzo [k]fluoranthene. The comparative compound 1-A is a compound having the basic skeleton according to this embodiment.

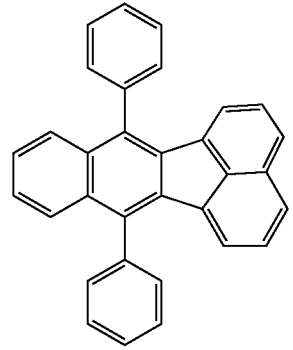 [SMILES: c1ccc(-c2c3c(c(-c4ccccc4)c4ccccc24)-c2cccc4cccc-3c24)cc1]

[R1]

The emission wavelength was measured by photoluminescence measurement of a diluted toluene solution at an excitation wavelength of 350 nm at room temperature using an F-4500 manufactured by Hitachi, Ltd. The reduction potential was determined by cyclic voltammetry (CV) measurement. The CV measurement was performed using a DMF solution of 0.1 M tetrabutylammonium perchlorate (for reduction potential measurement). The reference electrode was Ag/Ag⁺, the counter electrode was Pt, and the working electrode was glassy carbon. The scanning speed of voltage was 1.0 V/s. The measurement instrument was an electrochemical analyzer 660C manufactured by ALS. Table 1 shows the results.

TABLE 1

| Name of compound | Molecular structure | Maximum emission wavelength (nm) | Reduction potential (V) |
|---|---|---|---|
| Comparative compound R1 | 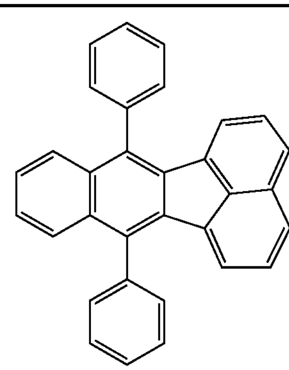 | 428 | −2.18 |

TABLE 1-continued

| Name of compound | Molecular structure | Maximum emission wavelength (nm) | Reduction potential (V) |
|---|---|---|---|
| Comparative compound 1-A | (structure shown) | 440 | −1.92 |

Table 1 shows that the maximum emission wavelength of the comparative compound R1 is not in a desired region, and the comparative compound R1 has a low reduction potential of −2.18 V. On the other hand, the comparative compound 1-A having the basic skeleton according to this embodiment has a maximum emission wavelength in a desired region. Therefore, the comparative compound 1-A is a light-emitting material having a high color purity while having a structure close to the basic skeleton. Accordingly, when a blue light emission color is optimized by introducing a substituent, the emission color can be optimized by introducing a small number of substituents compared with the case where a substituent is introduced to a benzo[k]fluoranthene that is a basic skeleton of the comparative compound RE Furthermore, vibrational deactivation is suppressed by the substituent, which increases the efficiency of the light-emitting element and increases the life.

The comparative compound 1-A having the basic skeleton according to this embodiment has a higher reduction potential than the comparative compound R1, which shows that the electron acceptability is improved. The basic skeleton according to this embodiment has a structure obtained by condensing two fluoranthene skeletons. Therefore, one partial structure having a 5π electron system is added. This shows that the basic skeleton has a structure in which the reduction potential is increased and the electron acceptability is improved.

(2) The ring Q has an electron-withdrawing cyano group and bonds to the basic skeleton at a position at which the electron orbital distribution of LUMO of the basic skeleton is relatively lower than that of HOMO.

Next, when the organic compound represented by the formula [1] is made, the present inventors have focused on the substitution position of a ring Q to be introduced to the basic skeleton.

As described above, the basic skeleton itself according to this embodiment is a stable compound having electron acceptability. When the basic skeleton has a structure that does not readily undergo a chemical change during continuous power application, an organic light-emitting element having higher driving durability can be provided. By introducing the ring Q having an electron-withdrawing cyano group to the basic skeleton, the electron acceptability is improved, which can further improve the charge stability.

At the same time, to prevent the deterioration of the color purity of blue light, the emission wavelength needs to be designed so as not to shift to longer wavelengths by introducing the ring Q to an appropriate position of the basic skeleton. The emission wavelength is shifted to shorter wavelengths by introducing the ring Q, and thus blue light with a higher color purity is emitted.

Herein, description will be made using, as an example, a compound having an acenaphtho[1,2-k]benzo[e]acenaphthophenanthrene skeleton that is the basic skeleton according to this embodiment. The comparative compounds 1-A and 1-B and the exemplary compound A1 according to the present disclosure, which are compounds having an acenaphtho[1,2-k]benzo[e]acenaphthophenanthrene skeleton, were compared with each other in terms of emission wavelength and reduction potential. Table 2 shows the results. The measurement methods of emission wavelength and reduction potential are as described above.

TABLE 2

| Name of compound | Molecular structure | Maximum emission wavelength (nm) | Reduction potential (V) |
|---|---|---|---|
| Comparative compound 1-A | 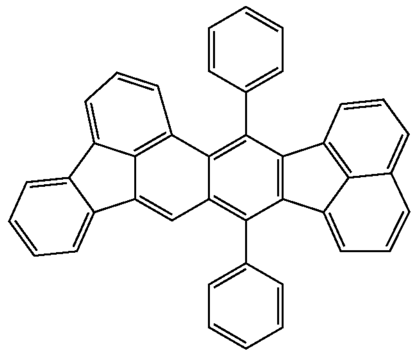 [SMILES: c1ccc(-c2c3cc4c5ccccc5c5cccc(c3c(-c3ccccc3)c3c6cccc7cccc(c23)c76)c54)cc1] | 440 | −1.92 |
| Comparative compound 1-B | 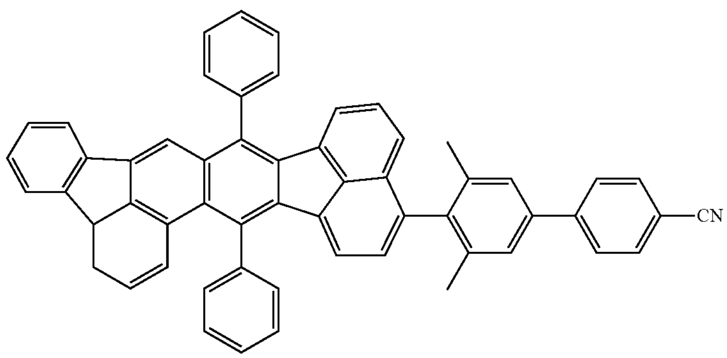 [SMILES: Cc1cc(-c2ccc(C#N)cc2)cc(C)c1-c1ccc2c3c(cccc13)-c1c-2c(-c2ccccc2)c2c3c4c(cc2c1-c1ccccc1)-c1ccccc1C4CC=C3] | 447 | −1.89 |
| Exemplary compound A1 | 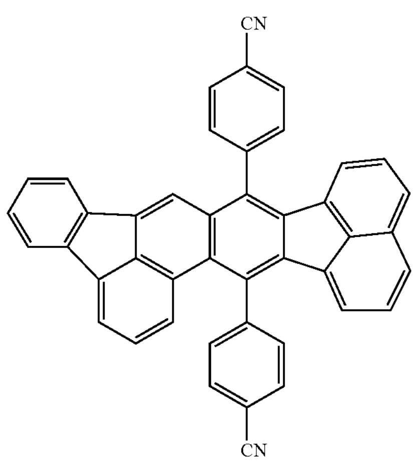 [SMILES: N#Cc1ccc(-c2c3cc4c5ccccc5c5cccc(c3c(-c3ccc(C#N)cc3)c3c6cccc7cccc(c23)c76)c54)cc1] | 438 | −1.84 |

The comparative compound 1-A is a compound in which a phenyl group having no electron-withdrawing substituent is introduced to the 9 and 16 positions of the acenaphtho[1,2-k]benzo[e]acenaphthophenanthrene skeleton instead of the ring Q. This is a compound in which the basic skeleton itself has characteristics close to those of the exemplary compound.

Table 2 shows that compared with the comparative compound 1-A, the comparative compound 1-B has a structure in which an aryl group having an electron-withdrawing cyano group is introduced to the 12 position of the acenaphtho[1,2-k]benzo[e]acenaphthophenanthrene skeleton serving as a basic skeleton. The comparative compound 1-B had a higher reduction potential of −1.89 V than the comparative compound 1-A because of its electron-withdrawing substituent effect, but had a maximum emission wavelength of 447 nm. The wavelength of the comparative compound 1-B shifts to longer wavelengths than the comparative compound 1-A, which deteriorates the color purity.

On the other hand, the exemplary compound A1 serving as a compound according to the present disclosure has a structure in which an aryl group having a cyano group (ring Q) is introduced to the 9 and 16 positions of the acenaphtho [1,2-k]benzo[e]acenaphthophenanthrene skeleton. The exemplary compound A1 had a higher reduction potential of −1.84 V than the comparative compound 1-A and also had a shorter maximum emission wavelength of 438 nm than the comparative compound 1-A. Thus, the exemplary compound A1 has a better color purity.

This result can be considered as follows. The electron orbital distributions of HOMO and LUMO of the acenaphtho[1,2-k]benzo[e]acenaphthophenanthrene skeleton are dependent on the positions of the acenaphtho[1,2-k]benzo[e]acenaphthophenanthrene skeleton. Therefore, the degree of effect on HOMO and LUMO is probably dependent on the positions to which an electron-withdrawing substituent is introduced.

In other words, at the 12 position of the acenaphtho[1,2-k]benzo[e]acenaphthophenanthrene skeleton, the electron orbital distribution of LUMO is higher than that of HOMO. Therefore, a relatively large electron withdrawing effect is exerted to LUMO and the optical band gap is narrowed. As a result, the maximum emission wavelength of the comparative compound 1-B is shifted to longer wavelengths than the comparative compound 1-A, and the color purity probably departs from the desired range of color purity.

On the other hand, the exemplary compound A1 serving as a compound according to the present disclosure has a structure in which an electron-withdrawing substituent is introduced to the 9 and 16 positions of the acenaphtho[1,2-k]benzo[e]acenaphthophenanthrene skeleton. At these positions, the electron orbital distribution of LUMO of the acenaphtho[1,2-k]benzo[e]acenaphthophenanthrene skeleton is relatively lower than that of HOMO. Therefore, a relatively large electron withdrawing effect is exerted to HOMO and the optical band gap is widened. Consequently, the maximum emission wavelength of the exemplary compound A1 is shifted to shorter wavelengths than that of the comparative compound 1-A. At the same time, the reduction potential is increased because of the electron-withdrawing effect on LUMO.

Figure 1B:
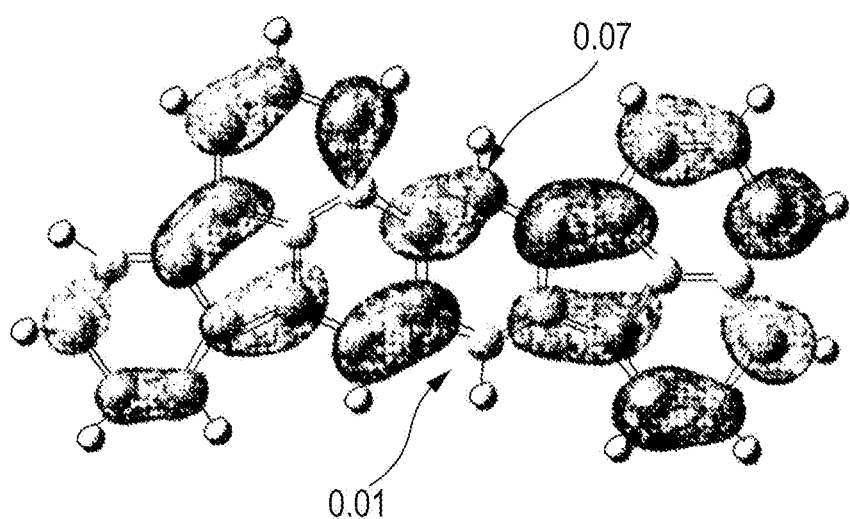

To support the above consideration, the electron orbital distributions of HOMO and LUMO of the acenaphtho[1,2-k]benzo[e]acenaphthophenanthrene skeleton were calculated and visualized using the molecular orbital calculations. FIGS. 1A and 1B illustrate the results. FIG. 1A illustrates the electron orbital distribution of HOMO, and FIG. 1B illustrates the electron orbital distribution of LUMO.

The density functional theory (DFT), which has been widely used today, was used as a calculation technique of the molecular orbital calculations. The functional was B3LYP and the basis function was 6-31G*. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.), which has been widely used today.

As is clear from FIGS. 1A and 1B, at the 9 and 16 positions of the acenaphtho[1,2-k]benzo[e]acenaphthophenanthrene skeleton, the electron orbital distribution of HOMO (FIG. 1A) is relatively higher than that of LUMO (FIG. 1B). The numerical values accompanied with arrows refer to an orbital coefficient. At the 9 and 16 positions of the acenaphtho[1,2-k]benzo[e]acenaphthophenanthrene skeleton, the orbital coefficient of HOMO is higher than that of LUMO.

Therefore, when an electron-withdrawing ring Q having a cyano group is introduced to the positions, the reduction potential is increased because of the electron-withdrawing effect on LUMO, but a larger electron-withdrawing effect is exerted to HOMO. As a result, the optical band gap is widened and the emission wavelength is shifted to shorter wavelengths.

(3) $R_4$ and $R_5$ Represent Groups Having No Lone Pair

The feature of the compound according to this embodiment is as follows. By introducing the ring Q having a cyano group to the 9 and 16 positions of the acenaphtho[1,2-k]benzo[e]acenaphthophenanthrene skeleton serving as a basic skeleton, the emission wavelength can be shifted to shorter wavelengths compared with the structure in which an aryl group having no electron-withdrawing substituent is introduced to the 9 and 16 positions. When $R_4$ and $R_5$ represent a hydrogen atom, this effect is produced as described above.

On the other hand, when $R_4$ and $R_5$ represent an aryl group, the group may have no lone pair. The difference in the effect of shortening the wavelength was investigated in terms of the presence or absence of lone pair in a group introduced to $R_4$ and $R_5$. Specifically, comparative compounds 1-C and 1-D that are compounds to which a group having a lone pair is introduced and a comparative compound 1-E and an exemplary compound A8 that are compounds to which a group having no lone pair is introduced are compared with each other. Table 3 shows the results.

TABLE 3

| Name of compound | Molecular structure | Maximum emission wavelength (nm) |
| --- | --- | --- |
| Comparative compound 1-C | 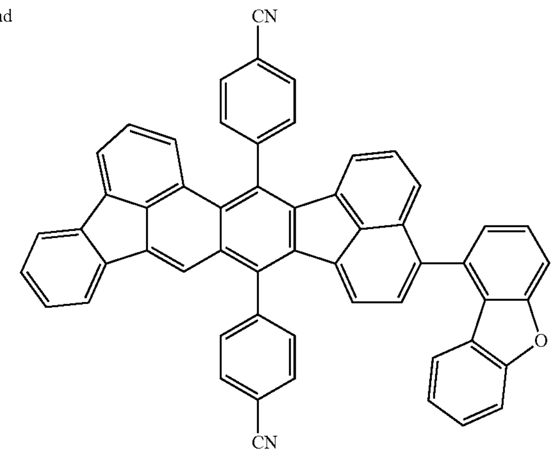 | 450 |
| Comparative compound 1-D | 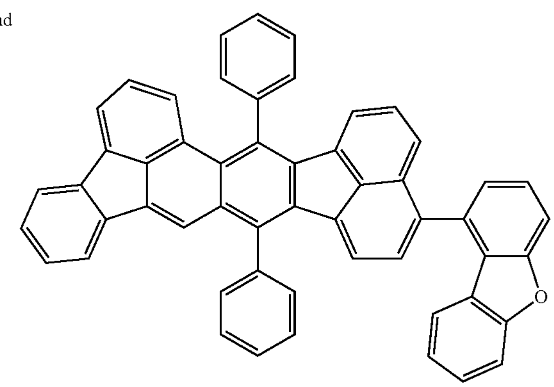 | 448 |
| Comparative compound 1-E | 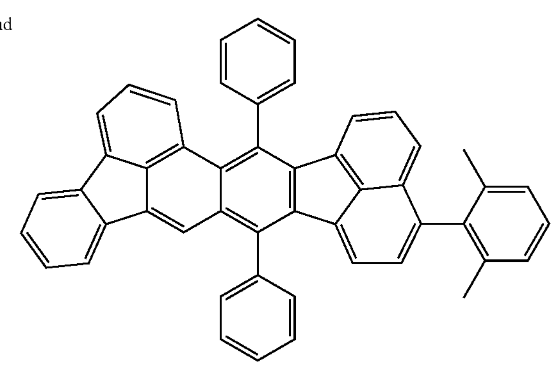 | 445 |

TABLE 3-continued

| Name of compound | Molecular structure | Maximum emission wavelength (nm) |
|---|---|---|
| Exemplary compound A8 | 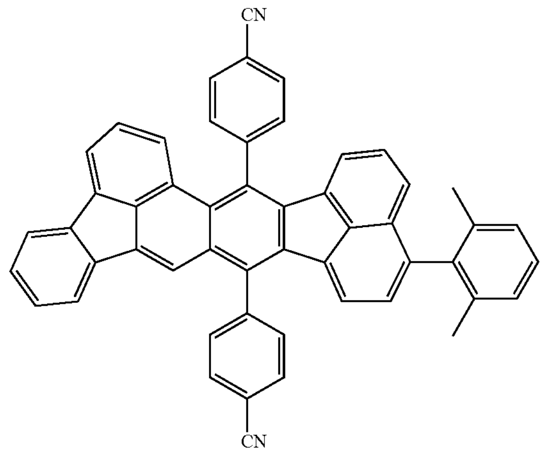 [SMILES: Cc1cccc(C)c1-c1ccc2c3c(-c4ccc(C#N)cc4)c4cc5c6ccccc6c6cccc(c4c(-c4ccc(C#N)cc4)c3c3cccc1c23)c65] | 443 |

The comparative compound 1-C is a compound in which dibenzofuran is introduced to $R_4$ of the exemplary compound A1. The comparative compound 1-D is a compound in which an unsubstituted phenyl group is introduced instead of the rings Q of the comparative compound 1-C. The maximum emission wavelength of the comparative compound 1-C is shifted to longer wavelengths by 2 nm than that of the comparative compound 1-D, which is an effect opposite to that of the present disclosure. The dibenzofuran introduced to $R_4$ has a lone pair on its oxygen atom, and the lone pair imparts electron-donating property. This selectively enhances the resonance effect on HOMO. The comparative compound 1-C to which a cyano group is introduced has a higher intramolecular charge transfer (CT) property than the comparative compound 1-D, and thus has a narrowed band gap. This cancels the effect of the present disclosure, which probably shifts the emission wavelength to longer wavelengths.

On the other hand, the emission wavelength of the exemplary compound A8 is shifted to shorter wavelengths than that of the comparative compound 1-E, which shows the effect of the present disclosure. Unlike the comparative compound 1-D, the substituent introduced to $R_4$ is a xylyl group having poor electron-donating property. Therefore, the electronic influence on HOMO and LUMO is not selective, which does not enhance the intramolecular CT property. This does not cancel the effect of the present disclosure, which probably shifts the emission wavelength to shorter wavelengths.

As described above, the organic compound according to this embodiment has the above features (1) and (2) and may have the above features (1) to (3). Therefore, the organic compound is a chemically stable organic compound that contributes to emitting blue light with a high color purity and has high electron acceptability. By using this organic compound, a high-efficiency organic light-emitting element that has high durability and emits blue light with a high color purity can be provided.

The organic compound according to the present disclosure will be specifically described below. However, the present disclosure is not limited thereto.

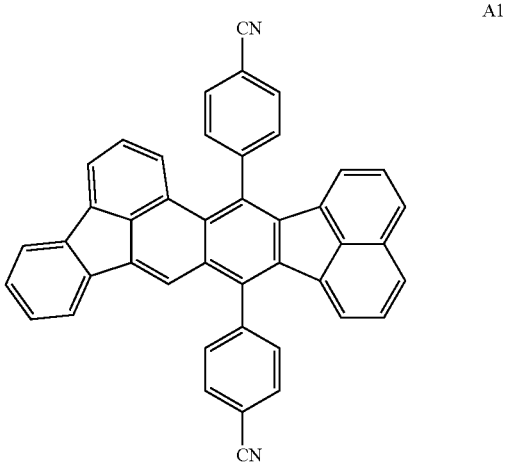

A1

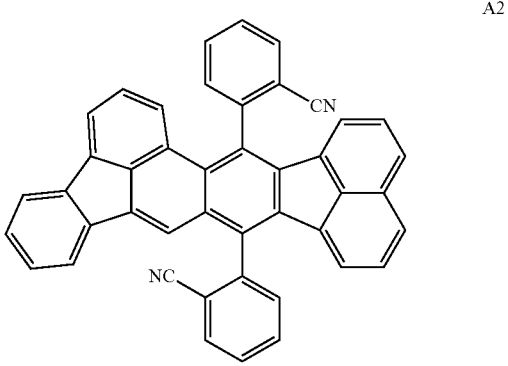

A2

-continued
A3
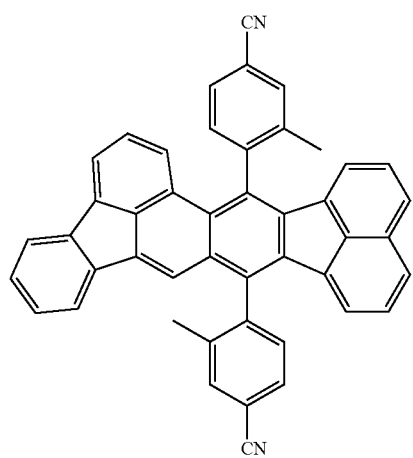
A4
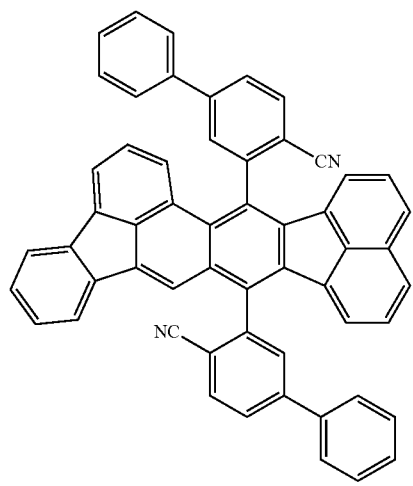
A5
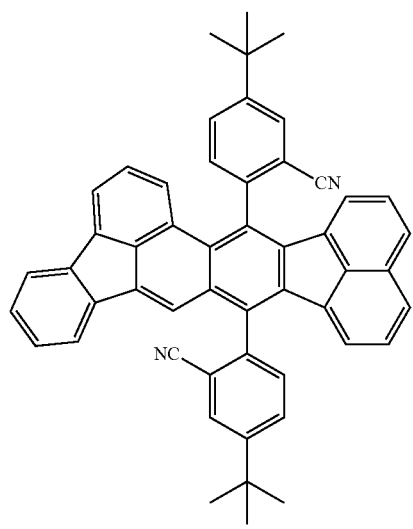
-continued
A6
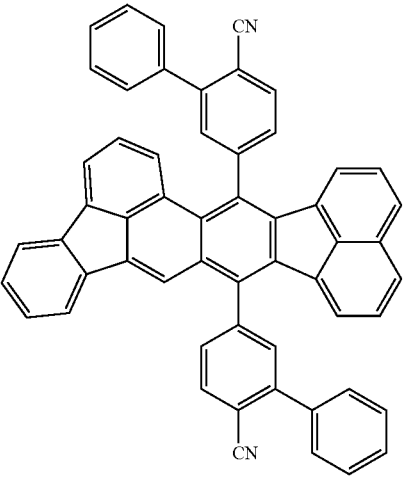
A7
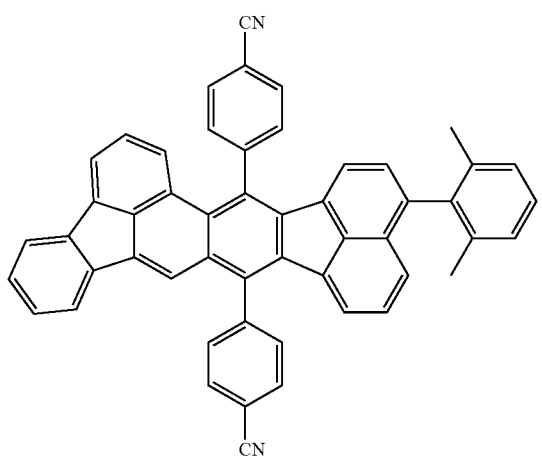
A8
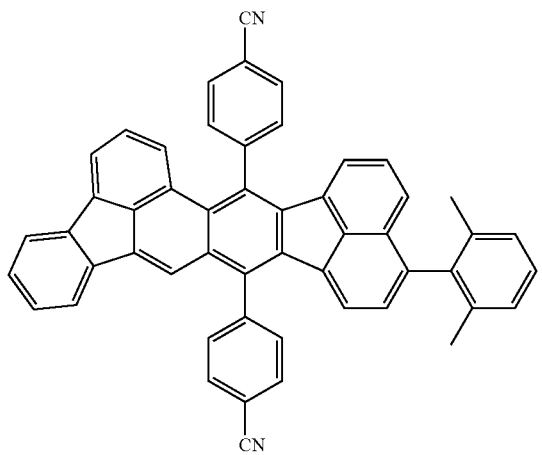

A9
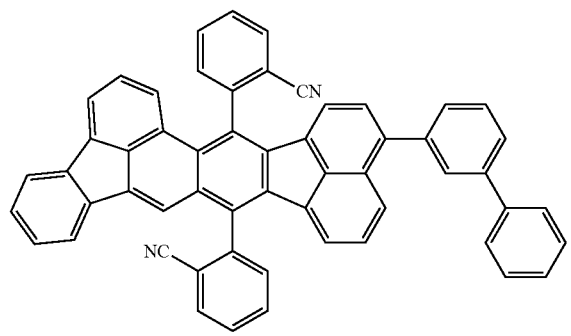
A10
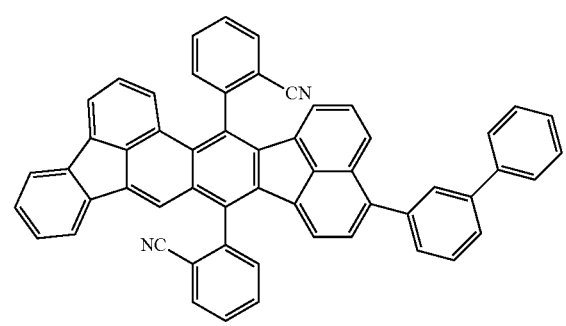
A11
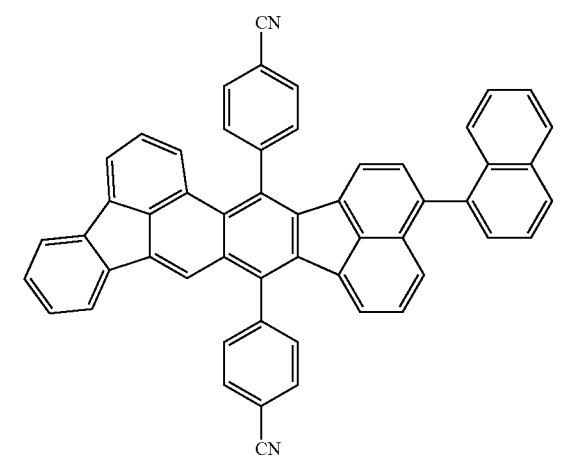
A12
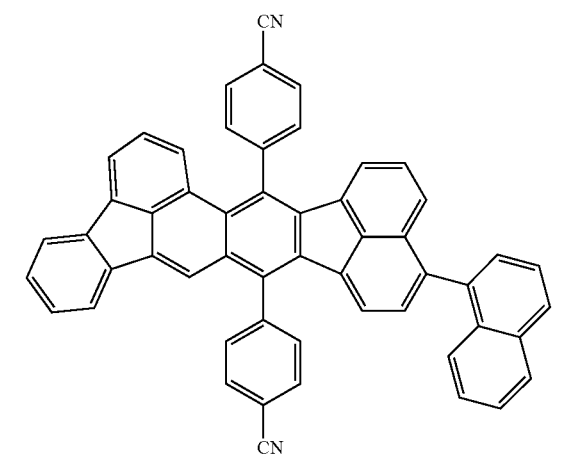
A13
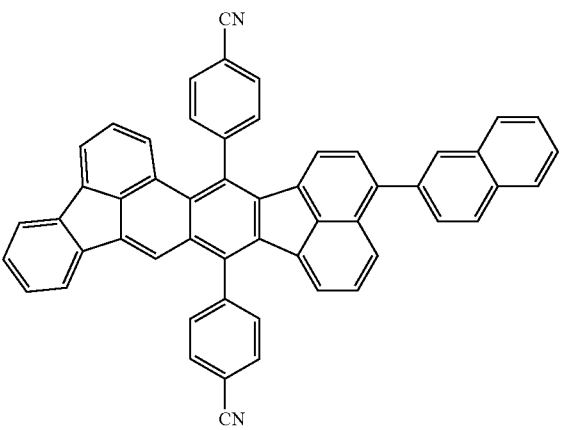
A14
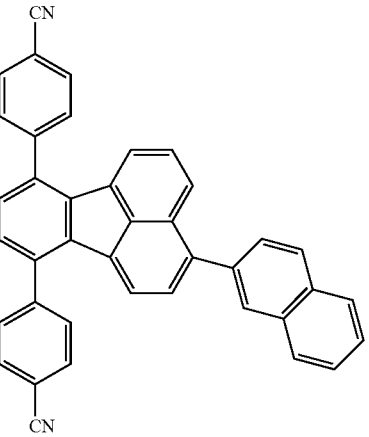
A15
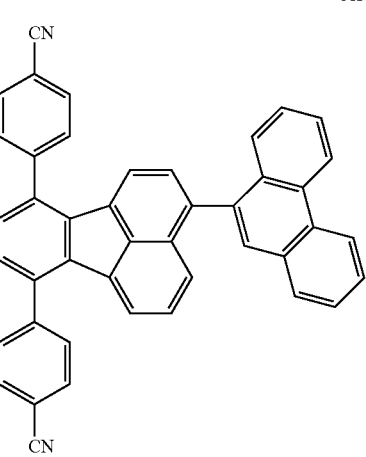

-continued
A16
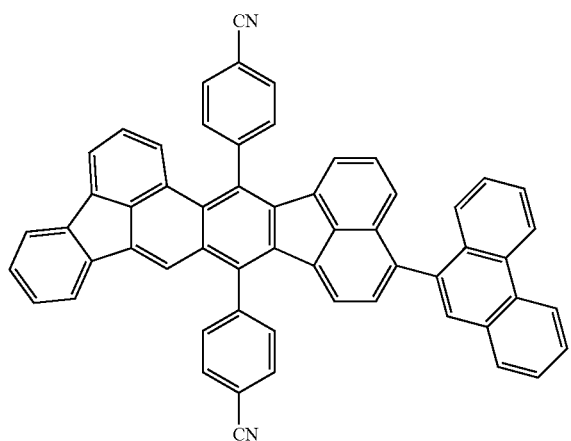
A17
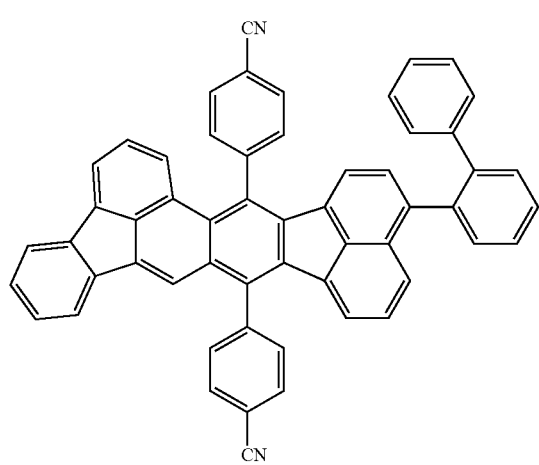
A18
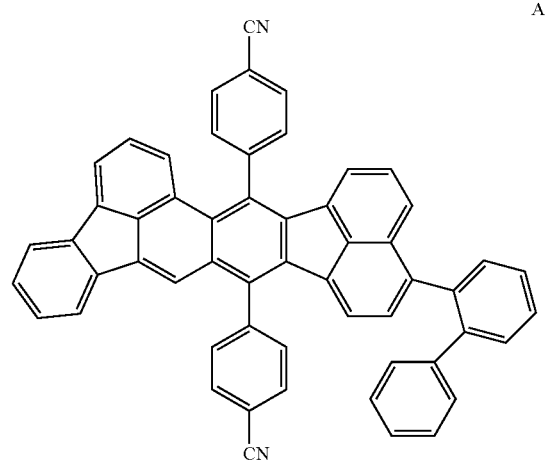
-continued
B1
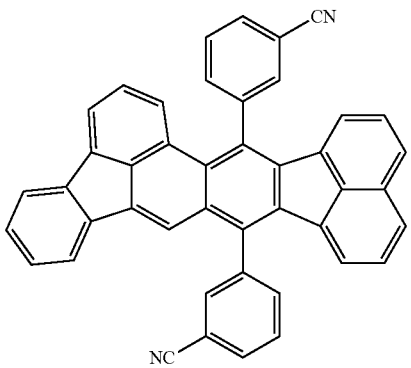
B2
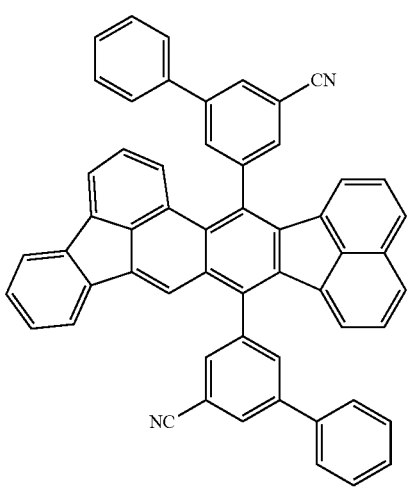
B3
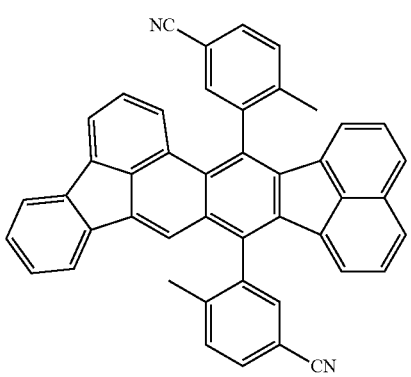
B4
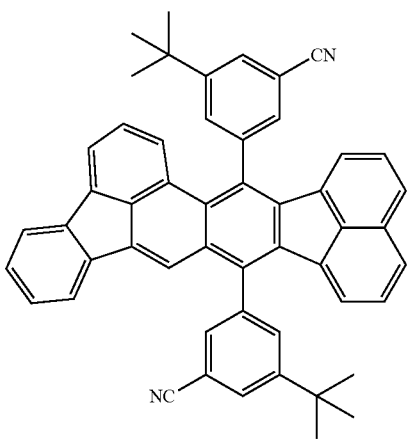

B5
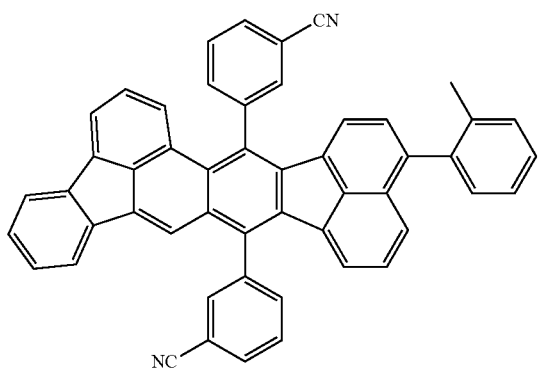
B6
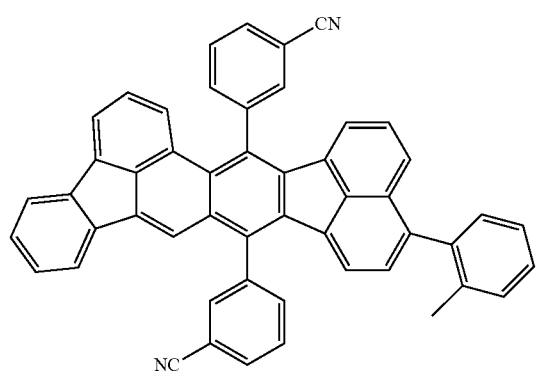
B7
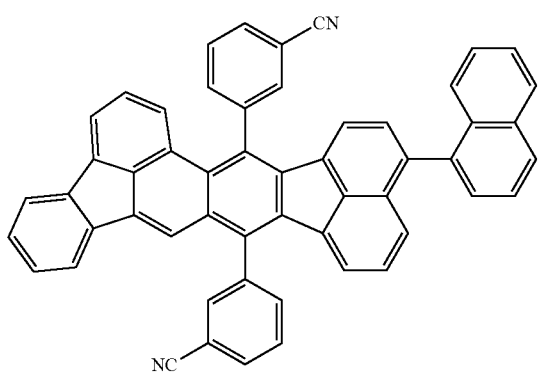
B8
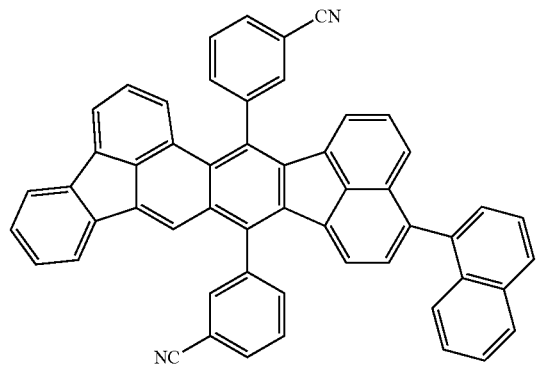
B9
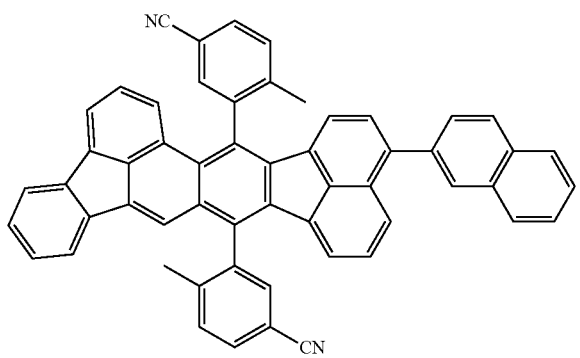
B10
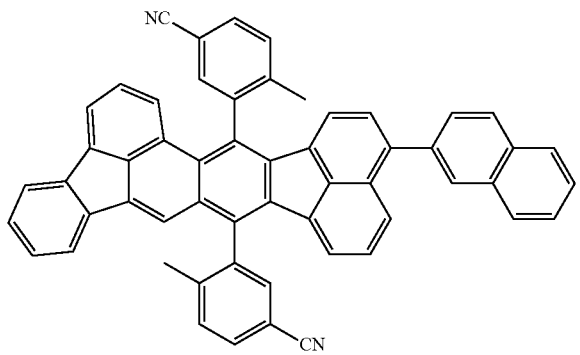
B11
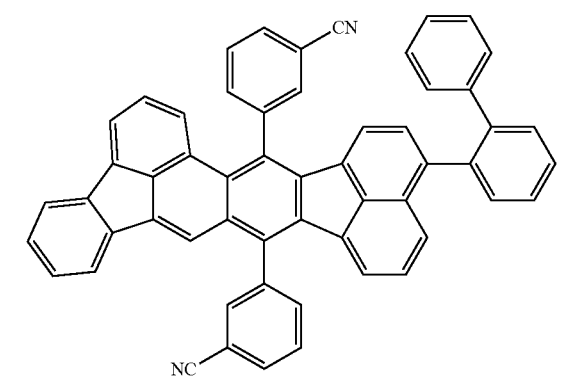
B12
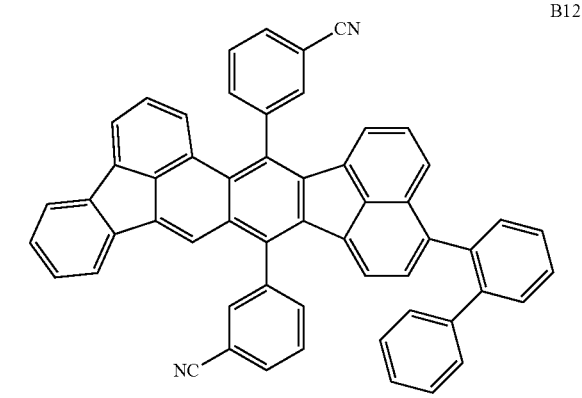

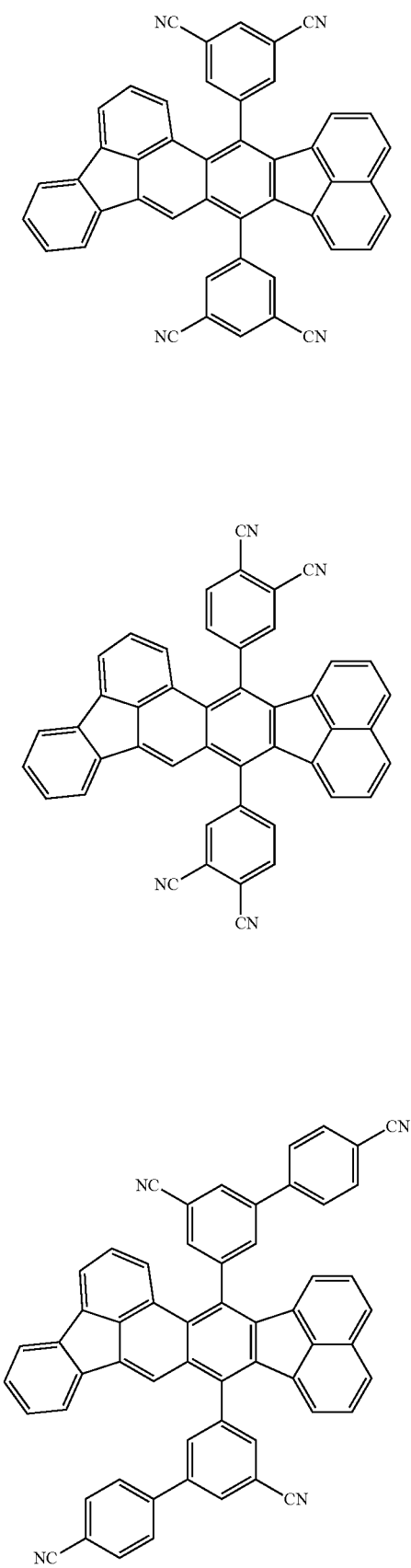

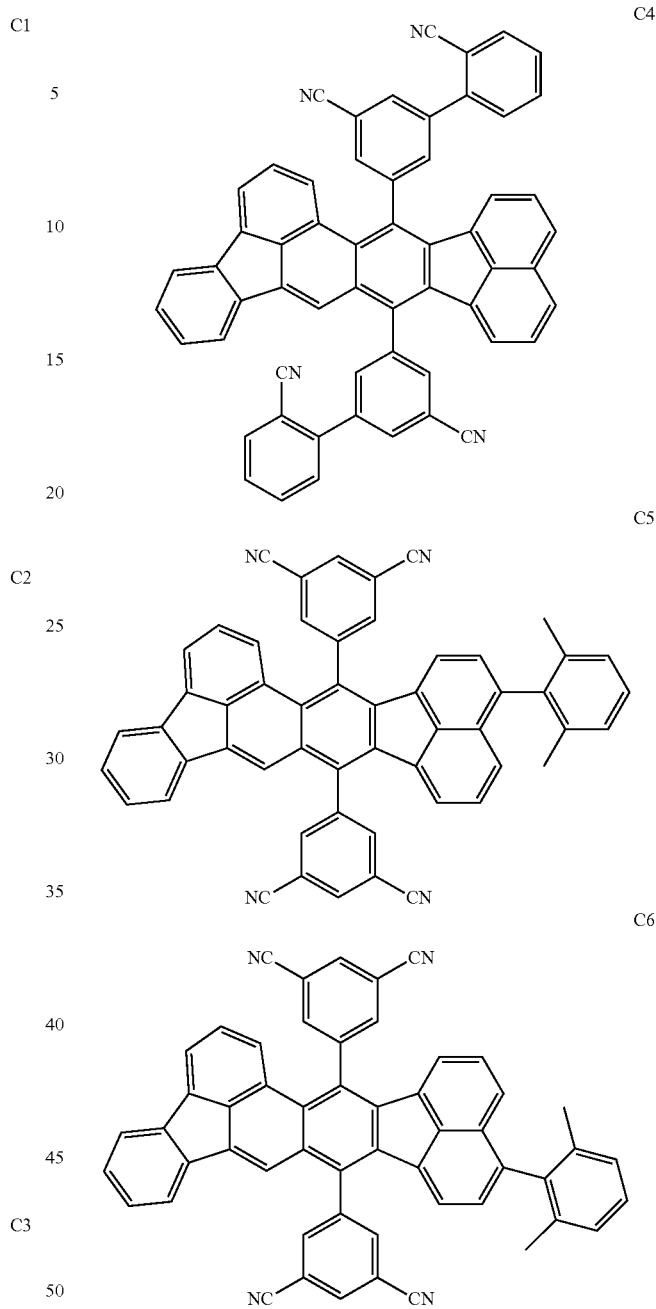

Among the exemplary compounds, the organic compounds that belong to the A group are compounds which are represented by the formula [2] and in which any of $R_6$ to $R_{10}$ and $R_{11}$ to $R_{15}$ represents a cyano group. When a substituent is introduced to $R_4$ or $R_5$, an aryl group having no lone pair and having 6 to 18 carbon atoms is introduced. This can achieve high electron acceptability and blue light emission with a high color purity.

Among the exemplary compounds, the organic compounds that belong to the B group are compounds that are represented by the formula [2] and in which $R_7$ or $R_9$ and $R_{12}$ or $R_{14}$ represent a cyano group. When a substituent is introduced to $R_4$ or $R_5$, an aryl group having no lone pair and having 6 to 18 carbon atoms is introduced. The organic compounds that belong to the B group have lower electron acceptability, but contribute to emitting blue light with a higher color purity than the organic compounds that belong to the A group. The organic compounds that belong to the B group may be compounds that are represented by the formula [2] and in which $R_7$ or $R_9$ and $R_{12}$ or $R_{14}$ among $R_6$ to $R_{15}$ represent a cyano group and the other substitution positions represent a hydrogen atom.

Among the exemplary compounds, the organic compounds that belong to the C group are compounds that are represented by the formula [2] and in which two of $R_7$ to $R_9$ and two of $R_{12}$ to $R_{14}$ represent a cyano group or a substituent having a cyano group as a substituent. When a substituent is introduced to $R_4$ or $R_5$, an aryl group having no lone pair and having 6 to 18 carbon atoms is introduced. The organic compounds that belong to the C group have higher electron acceptability than the organic compounds that belong to the A group, and contribute to emitting blue light with a high color purity.

The organic compound according to this embodiment is a compound that is suitable for blue light emission and has high chemical stability. Therefore, when the organic compound according to this embodiment is used as a material for organic light-emitting elements, an organic light-emitting element that has good light-emitting properties and high durability can be provided.

Organic Light-Emitting Element

Next, an organic light-emitting element according to this embodiment will be described. The organic light-emitting element according to this embodiment at least includes an anode and a cathode, which are a pair of electrodes, and an organic compound layer disposed between the electrodes. In the organic light-emitting element according to this embodiment, the organic compound layer may have a single-layer structure or a multilayer structure including a plurality of layers as long as the organic compound layer includes a light-emitting layer. When the organic compound layer has a multilayer structure including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may have a single-layer structure or a multilayer structure including a plurality of layers.

In the organic light-emitting element according to this embodiment, the organic compound according to this embodiment is contained in at least one layer of the organic compound layer. Specifically, the organic compound according to this embodiment is contained in any of the light-emitting layer, the hole injection layer, the hole transport layer, the electron blocking layer, the hole/exciton blocking layer, the electron transport layer, and the electron injection layer. The organic compound according to this embodiment may be contained in the light-emitting layer.

In the organic light-emitting element according to this embodiment, when the organic compound according to this embodiment is contained in the light-emitting layer, the light-emitting layer may be a layer formed of only the organic compound according to this embodiment or may be a layer formed of the organic compound according to this embodiment and other compounds. When the light-emitting layer is a layer formed of the organic compound according to this embodiment and other compounds, the organic compound according to this embodiment may be used as a host of the light-emitting layer or a guest of the light-emitting layer. Alternatively, the organic compound may be used as an assist material that can be contained in the light-emitting layer. Herein, the host refers to a compound having the highest mass ratio among the compounds that form the light-emitting layer. The guest refers to a compound that has a lower mass ratio than the host and that is responsible for main light emission among the compounds that form the light-emitting layer. The assist material refers to a compound that has a lower mass ratio than the host and that assists light emission of the guest among the compounds that form the light-emitting layer. The assist material is also referred to as a second host.

When the organic compound according to this embodiment is used as a guest of the light-emitting layer, the concentration of the guest is preferably 0.01 mass % or more and 20 mass % or less and more preferably 0.1 mass % or more and 5 mass % or less relative to the whole light-emitting layer.

When the organic compound according to this embodiment is used as a guest of the light-emitting layer, a material having a higher LUMO energy level than the organic compound according to this embodiment (a material having a LUMO energy level closer to the vacuum level) may be used as the host. This is because when a material having a higher LUMO energy level than the organic compound according to this embodiment having high electron acceptability, that is, a low LUMO energy level is used as the host, the organic compound according to this embodiment can accept a larger amount of electrons supplied to the host of the light-emitting layer.

As a result of thorough studies, the present inventors have found that when the organic compound according to this embodiment is used as the host or guest of the light-emitting layer, in particular, as the guest of the light-emitting layer, an element that produces an optical output with high efficiency and high luminance and that has very high durability is provided. This light-emitting layer may have a single-layer structure or a multilayer structure, or an emission color of this embodiment can be mixed with another color by adding a light-emitting material having another emission color. The multilayer structure refers to a state in which the light-emitting layer and another light-emitting layer are stacked. In this case, the emission color of the organic light-emitting element is not limited to blue. The emission color may be specifically white or an intermediate color. In the case of white, the other light-emitting layer emits light having a color other than blue, such as red or green. The light-emitting layers are formed by a method such as vapor deposition or coating. The details of the method will be specifically described in Examples below.

The organic compound according to this embodiment can be used as a material for organic compound layers other than the light-emitting layer that constitute the organic light-emitting element according to this embodiment. Specifically, the organic compound may be used as a material for, for example, electron transport layers, electron injection layers, hole transport layers, hole injection layers, and hole blocking layers. In this case, the emission color of the organic light-emitting element is not limited to blue. The emission color may be specifically white or an intermediate color.

The organic compound according to this embodiment may be used in combination with, for example, a publicly known low-molecular-weight or high-molecular-weight compound such as a hole injection or transport compound, a compound serving as the host, a luminous compound, or an electron injection or transport compound if necessary. Examples of these compounds will be described below.

A hole injection or transport material may be a material having a high hole mobility such that injection of holes from the anode is facilitated and the injected holes can be transported to the light-emitting layer. The hole injection or transport material may also be a material having a high glass transition temperature in order to suppress the deterioration of the film quality, such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer. Non-limiting specific examples of the compound used as the hole injection or transport material are shown below.

HT1

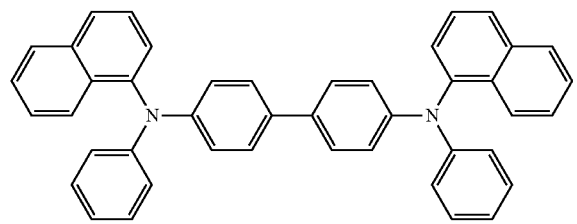

HT2

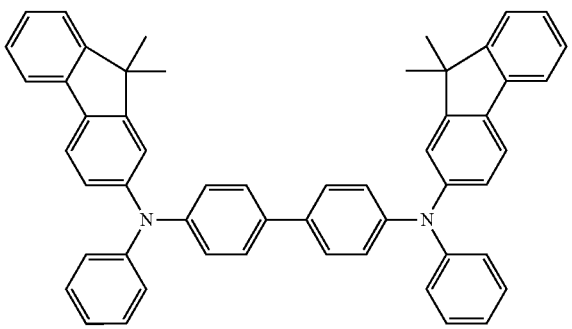

HT3

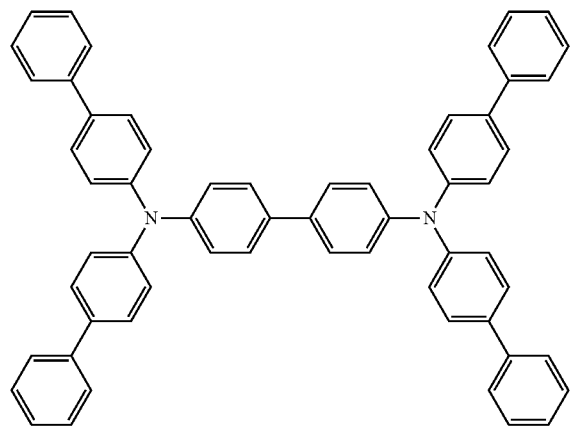

HT4

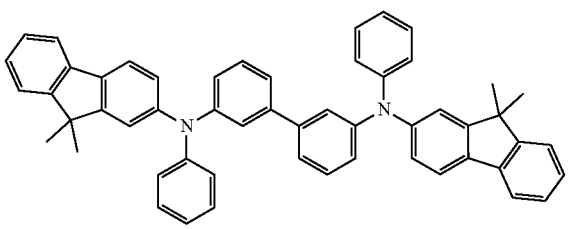

HT5

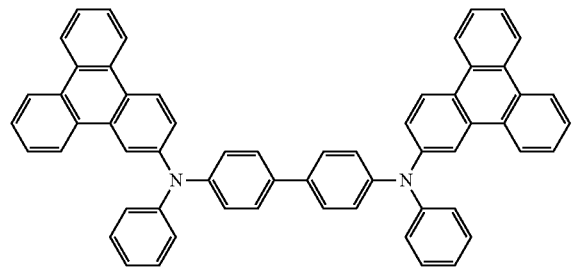

HT6

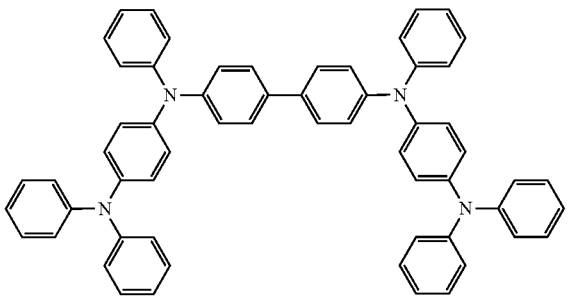

-continued
HT7
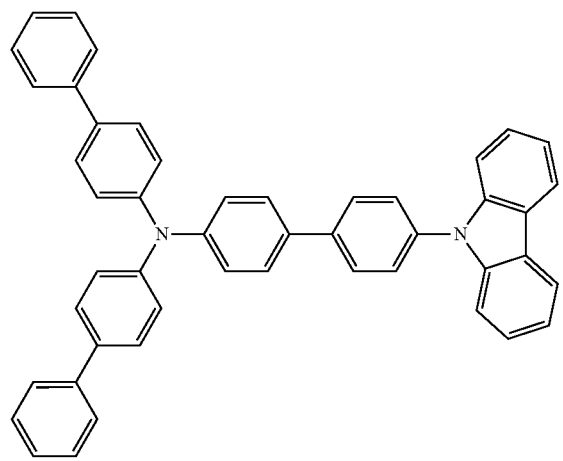
HT8
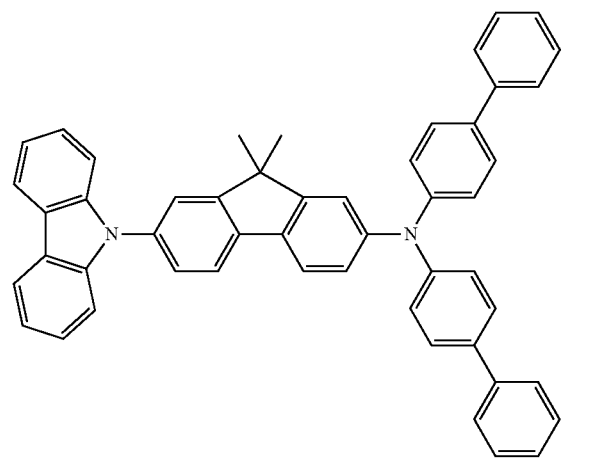
HT9
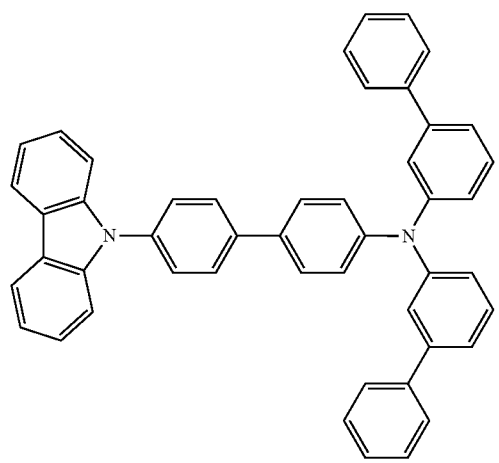
HT10
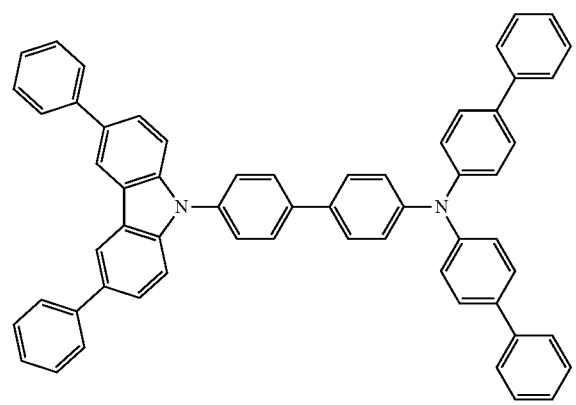
HT11
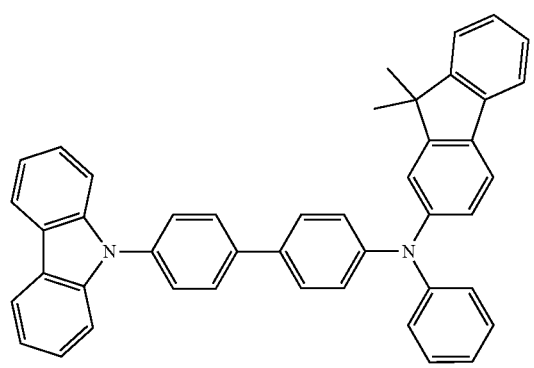
HT12
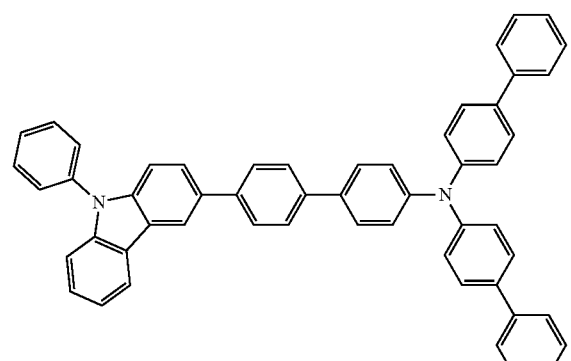

-continued

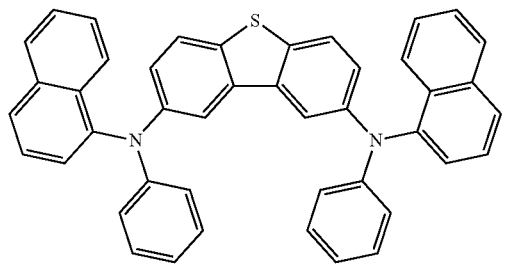
HT13

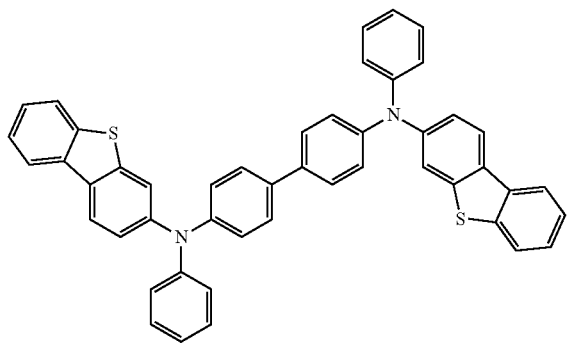
HT14

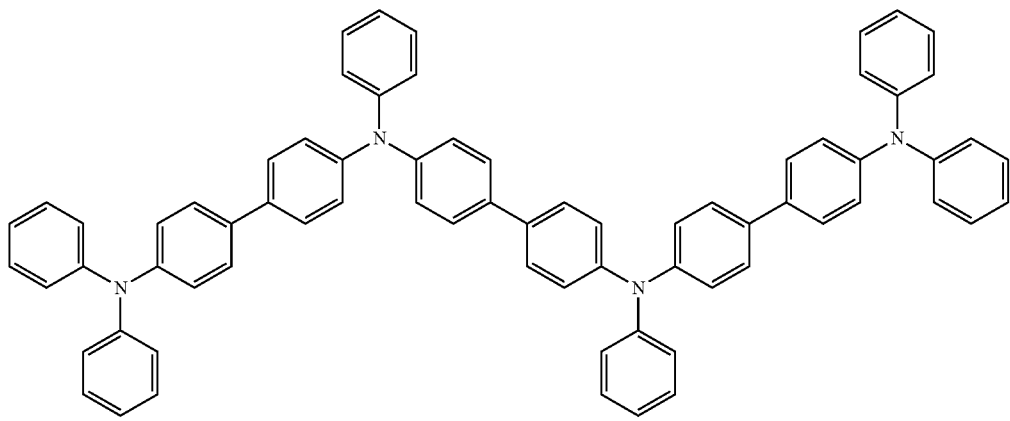
HT15

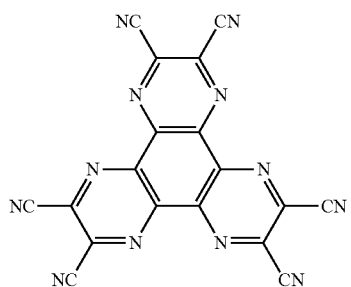
HT16

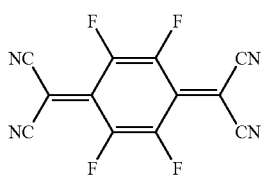
HT17

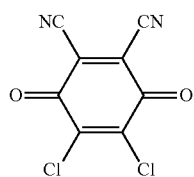
HT18

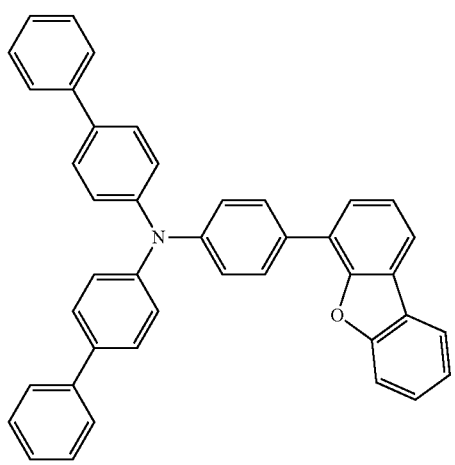
HT19

Examples of the light-emitting material mainly concerned with a light-emitting function include, in addition to the organic compound represented by the formula [1], fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives. Non-limiting specific examples of the compound used as the light-emitting material are shown below.

BD1

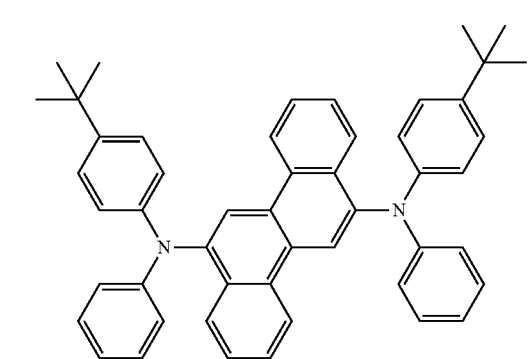

BD2

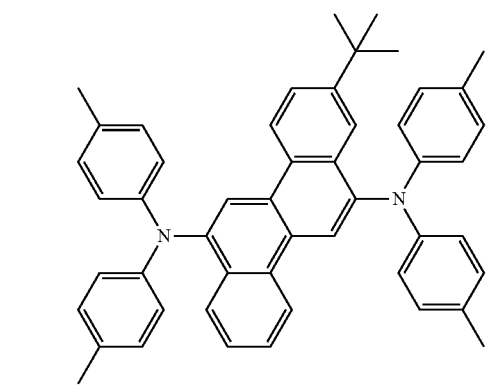

BD3

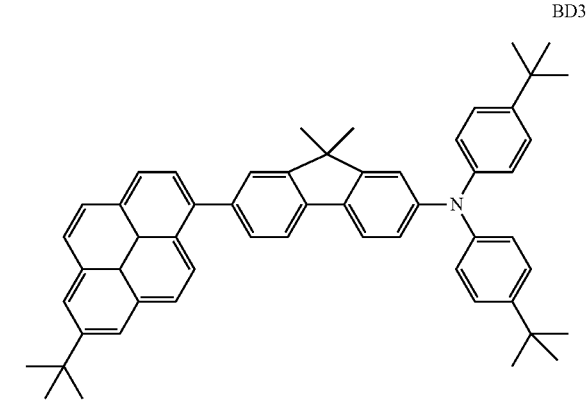

BD4

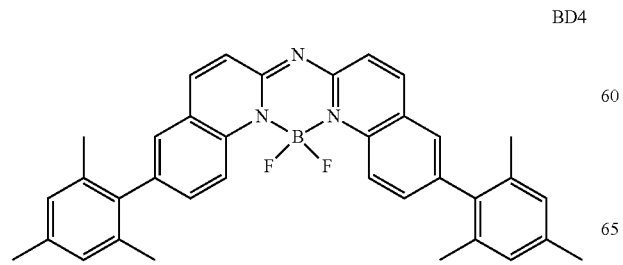

BD5

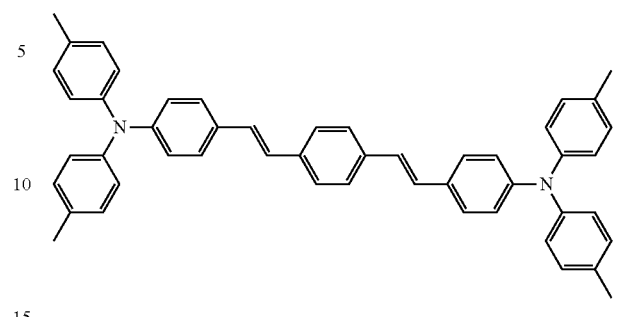

BD6

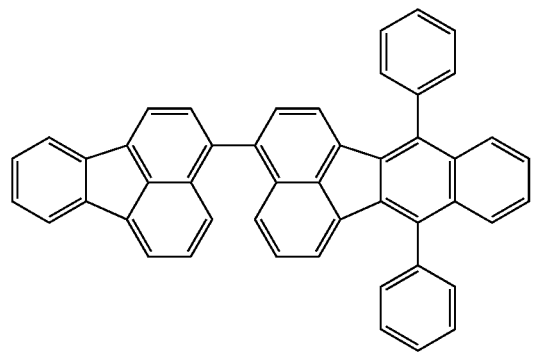

BD7

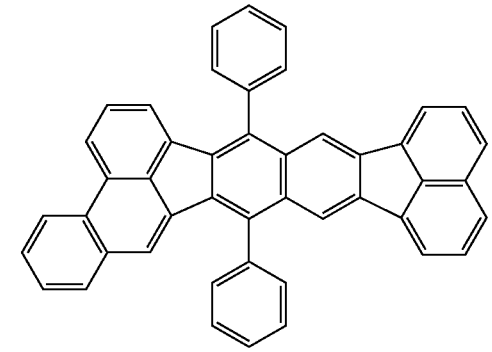

BD8

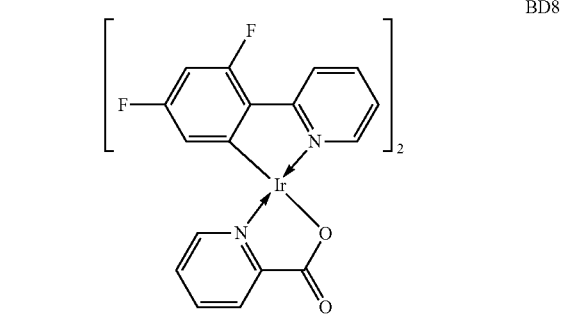

-continued
GD1
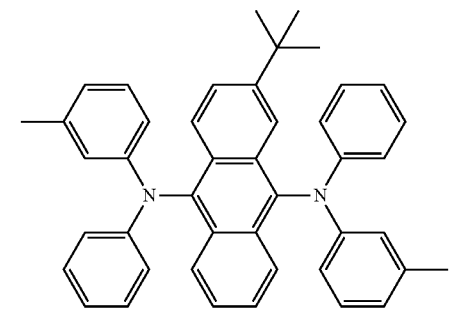
GD2
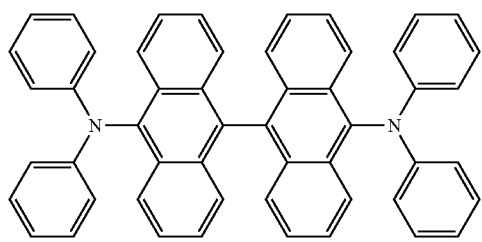
GD3
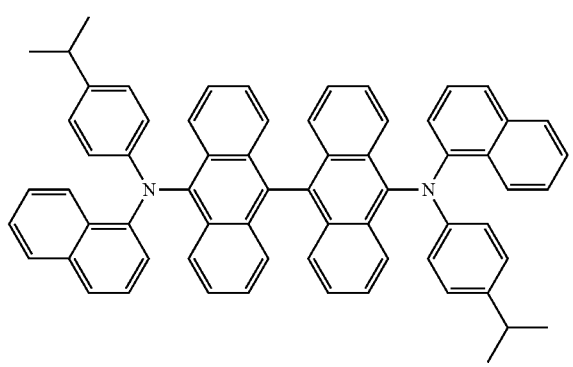
GD4
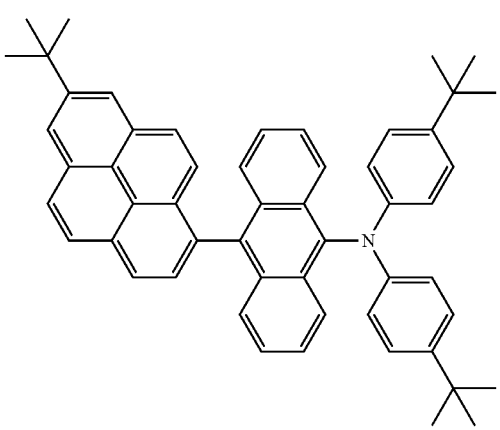
GD5
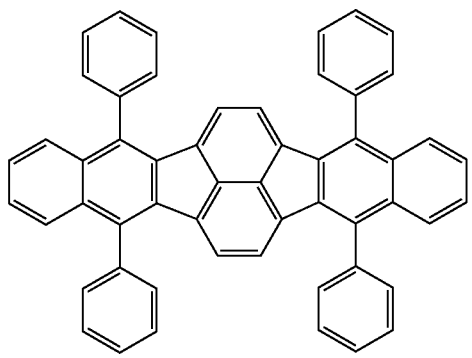
GD6
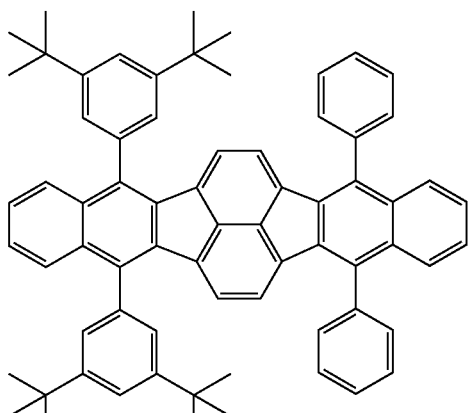
GD7
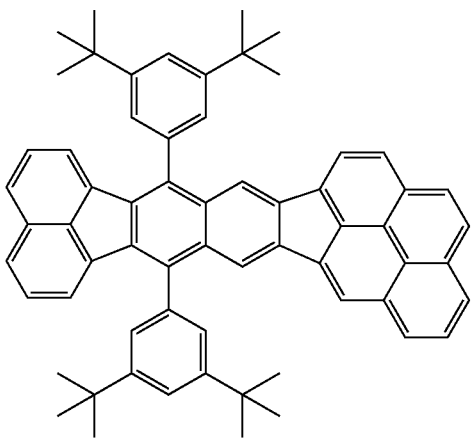

-continued
GD8
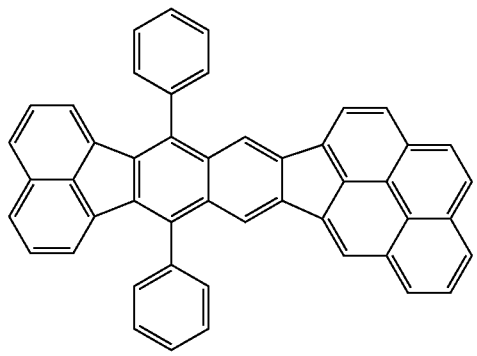
GD9
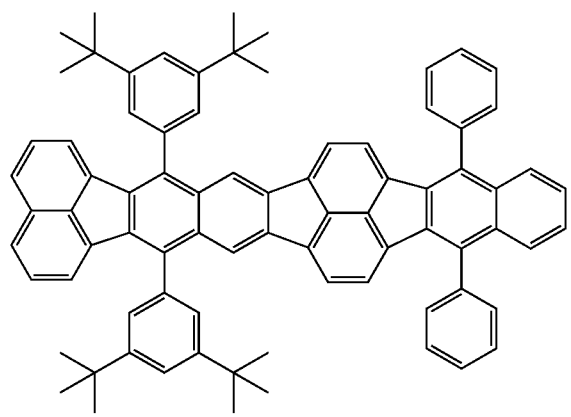
GD10
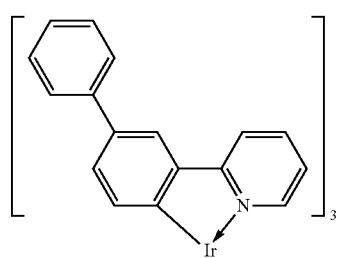
GD11
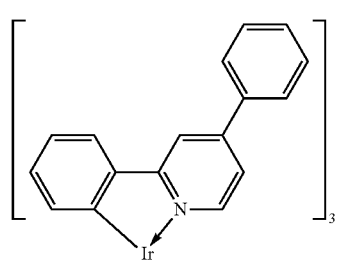
-continued
RD1
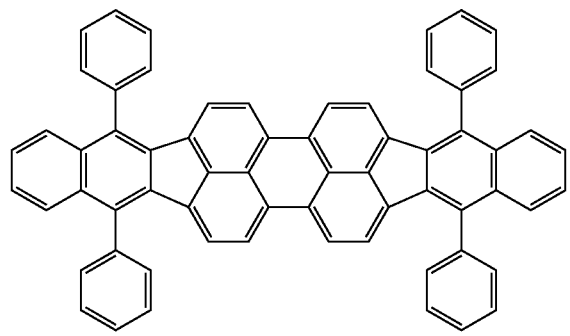
RD2
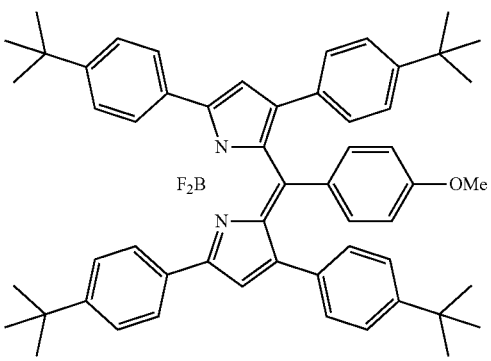
RD3
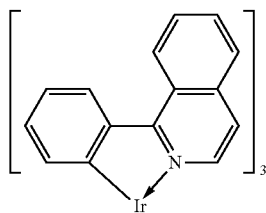
RD4
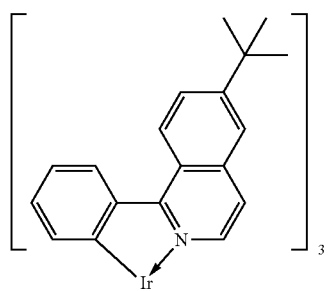
RD5
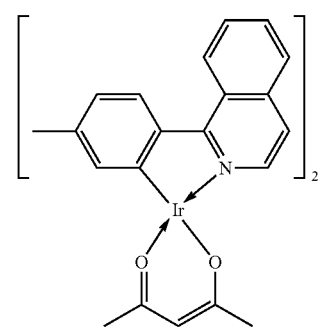
GD12

RD6

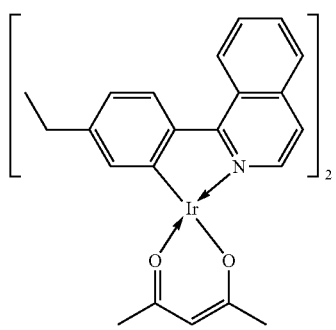

RD7

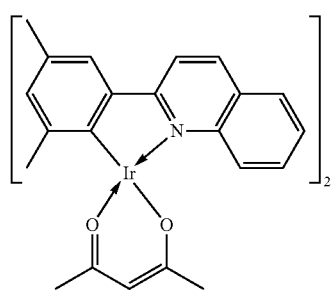

RD8

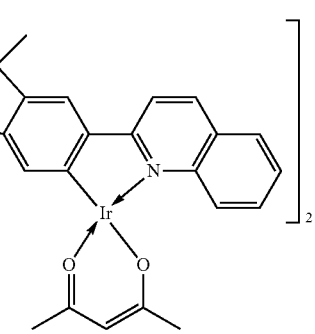

Examples of the light-emitting-layer host or light emission assist material contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes. Non-limiting specific examples of the compound used as the light-emitting-layer host or light emission assist material contained in the light-emitting layer are shown below.

EM1

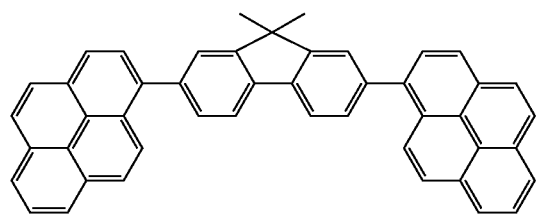

EM2

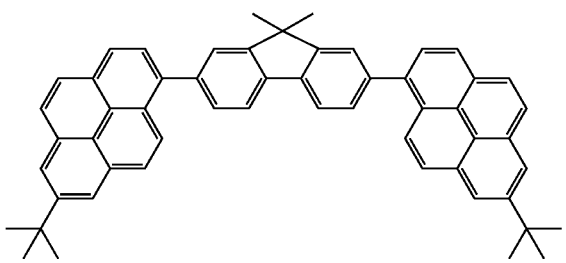

EM3

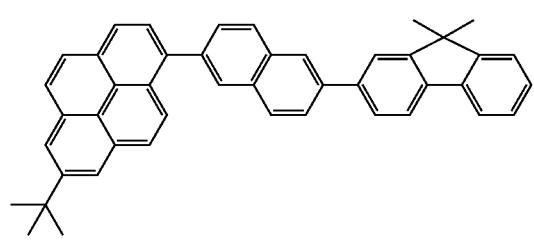

EM4

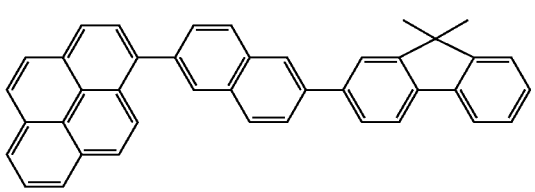

EM5

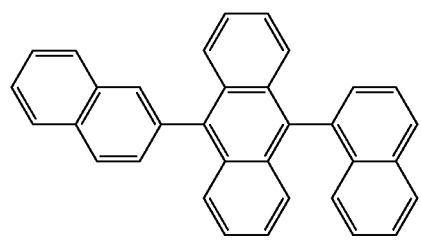

EM6

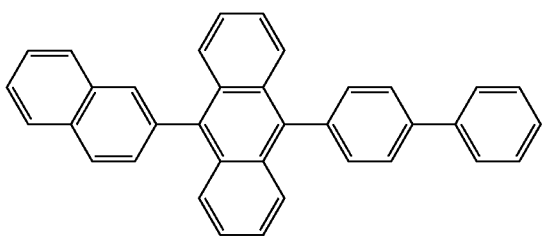

-continued
EM7
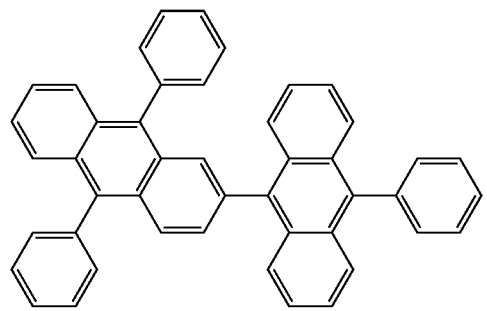
EM8
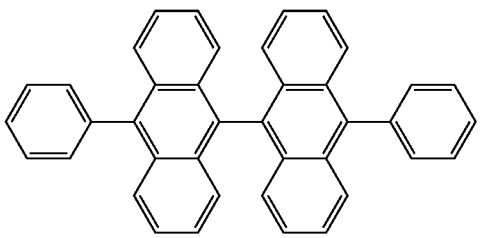
EM9
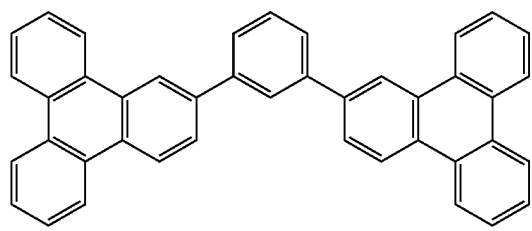
EM10
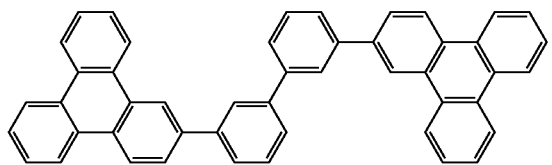
EM11
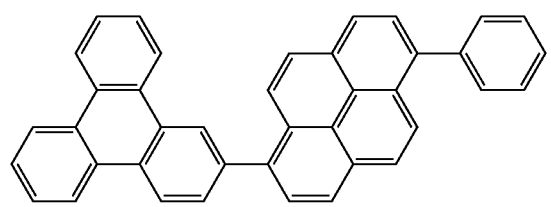
EM12
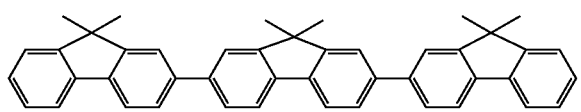
EM13
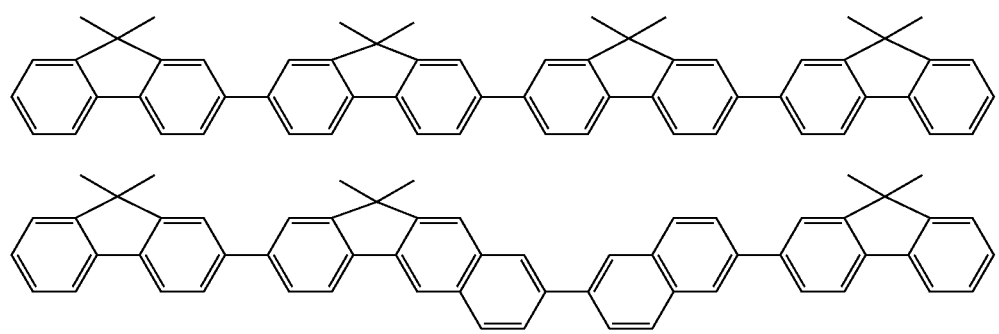
EM14
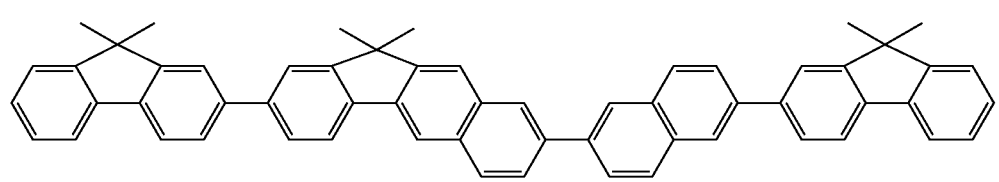
EM15
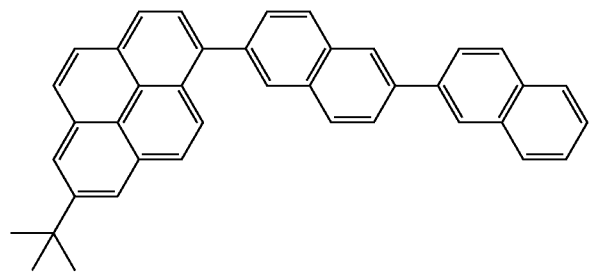
EM16
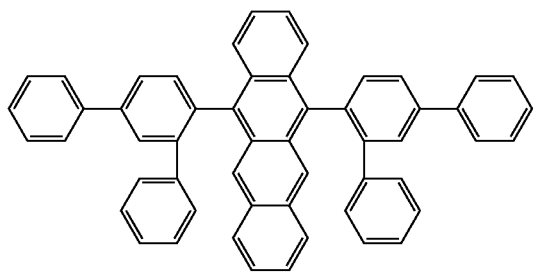

-continued
EM17
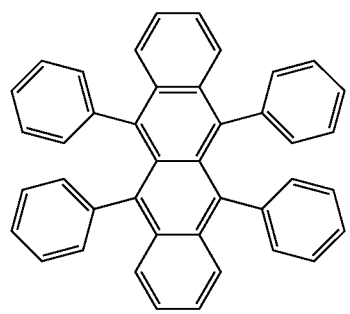
EM18
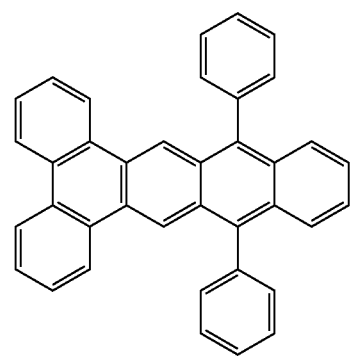
EM19
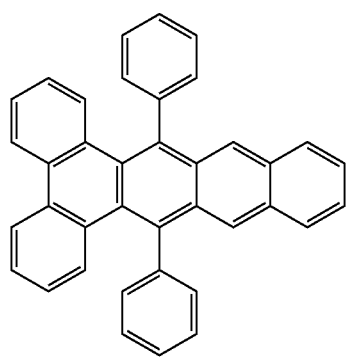
EM20
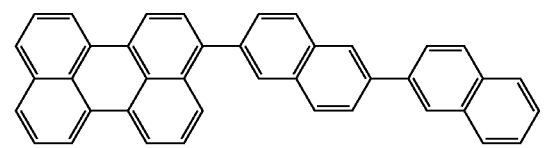
EM21
EM22
EM23
EM24

-continued
EM25
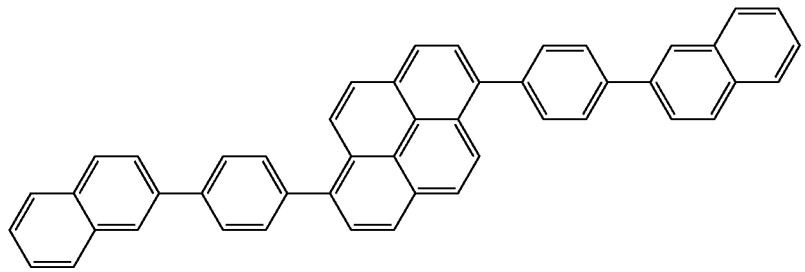
EM26
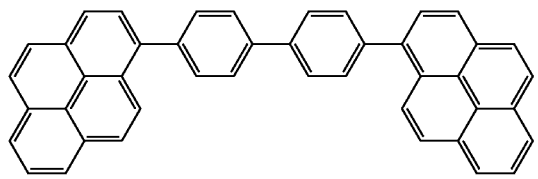
EM27
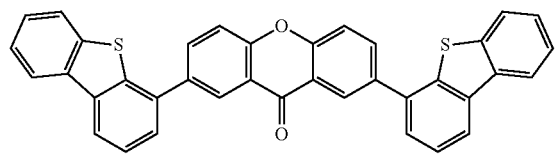
EM28
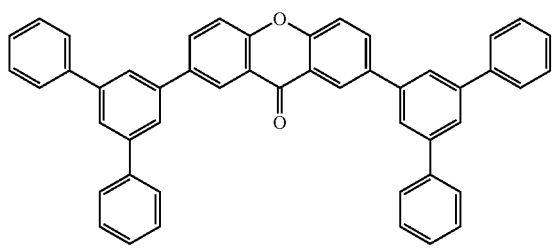
EM29
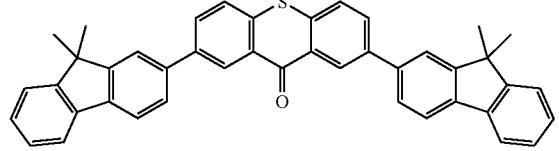
EM30
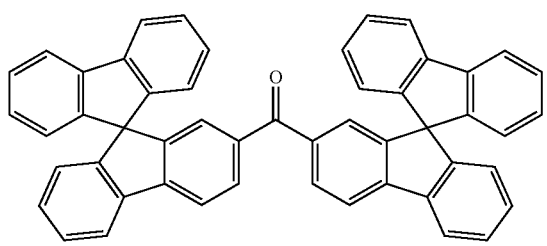
EM31
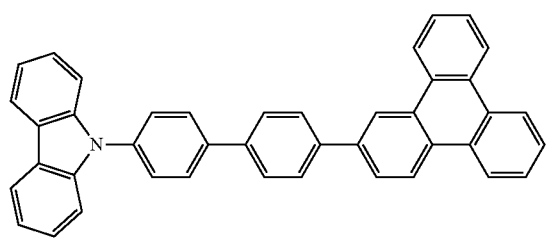
EM32
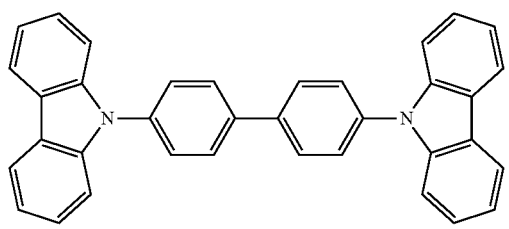
EM33
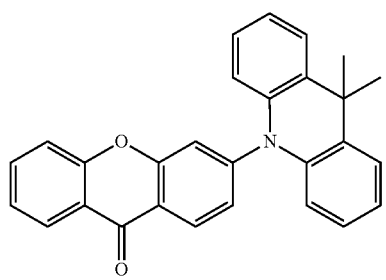

-continued

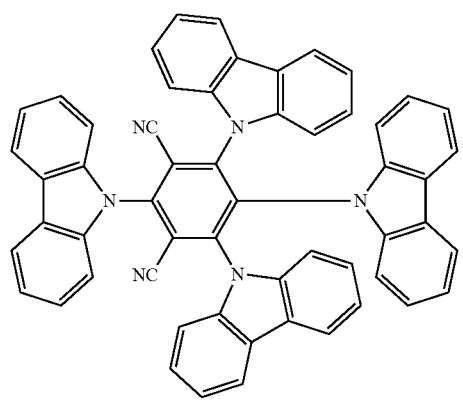
EM34

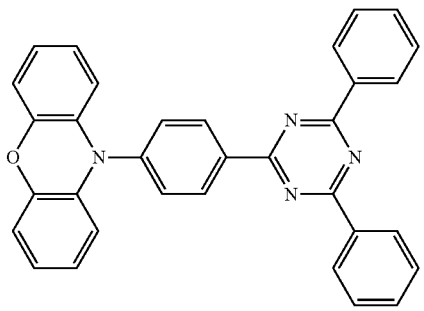
EM35

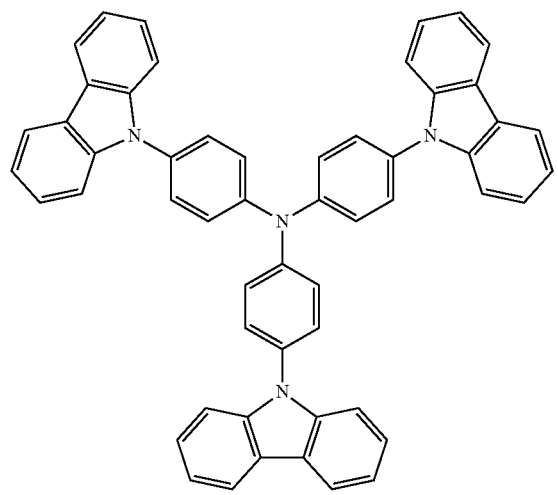
EM36

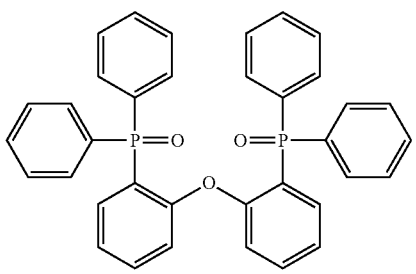
EM37

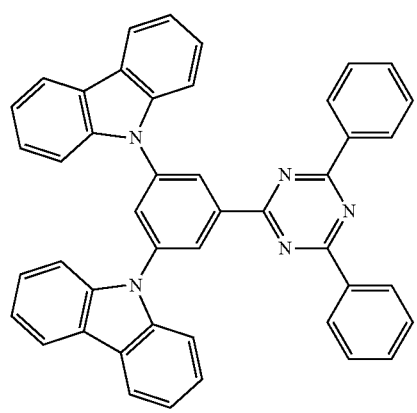
EM38

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer. Non-limiting specific examples of the compound used as the electron transport material are shown below.

ET1
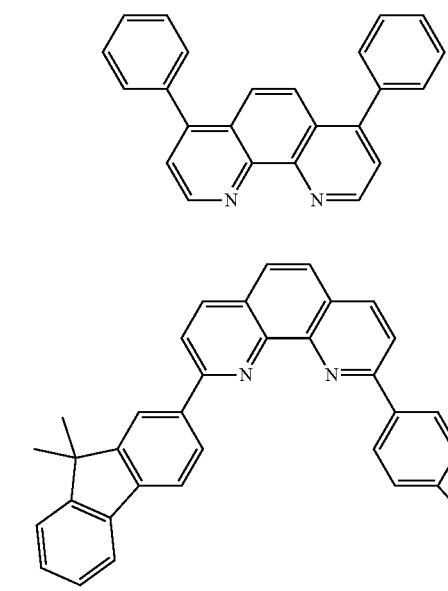
ET2
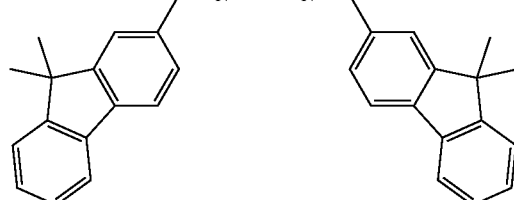
ET3
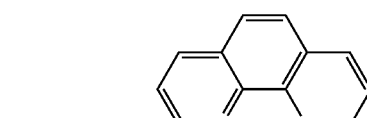
ET4
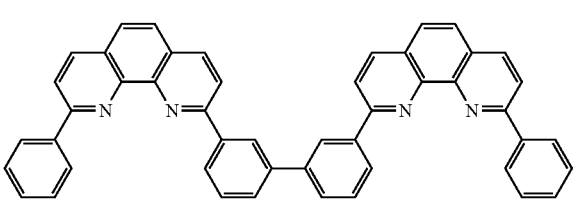
ET5
ET6
ET7
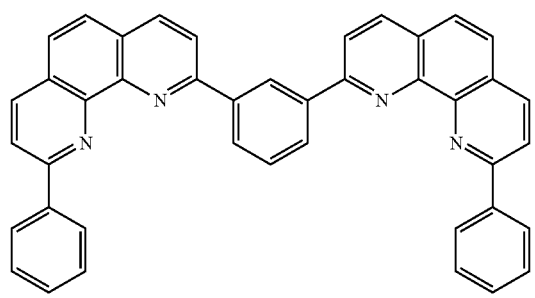
ET8
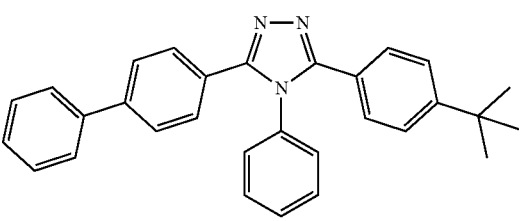
ET9
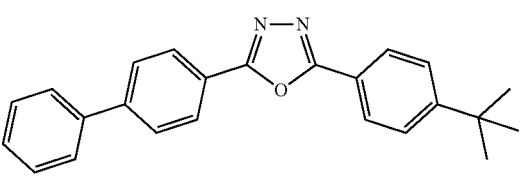
ET10
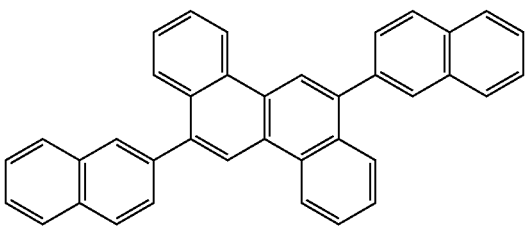
ET11
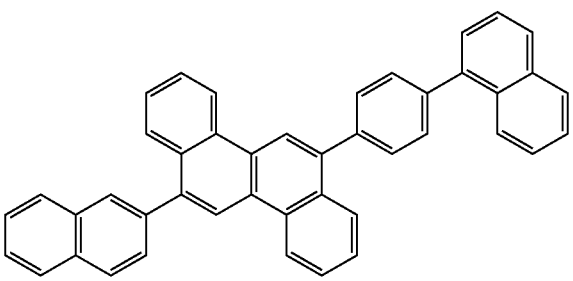
ET12
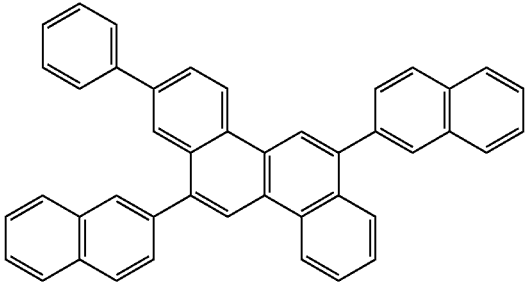

ET13
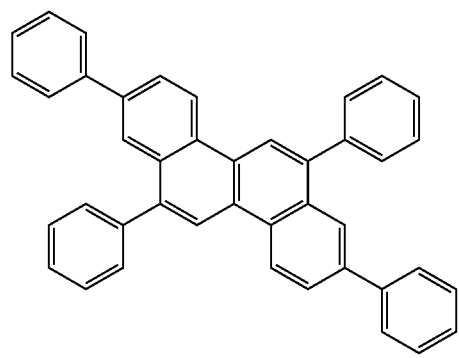
ET14
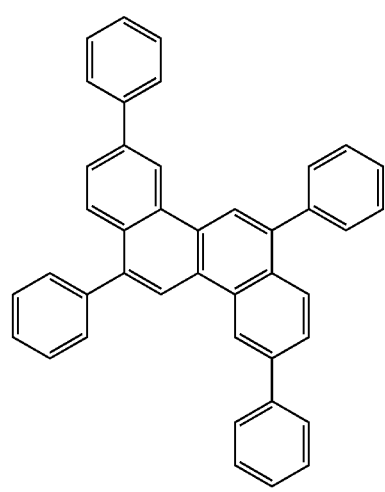
ET15
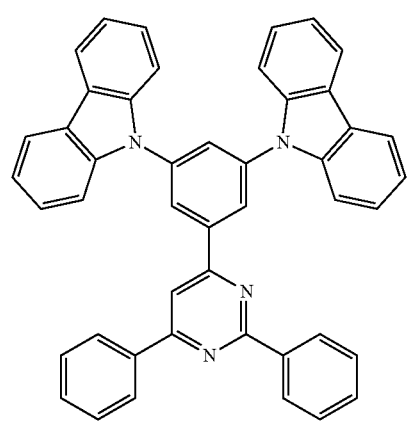
ET16
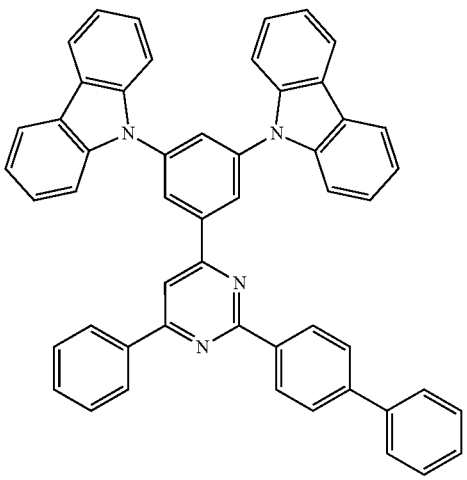
ET17
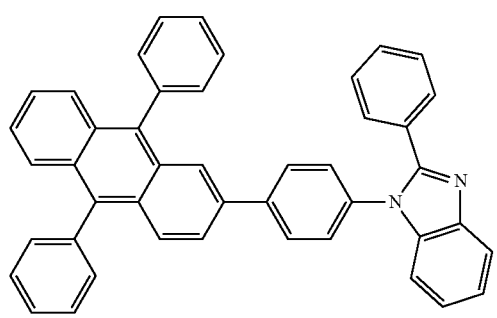
ET18
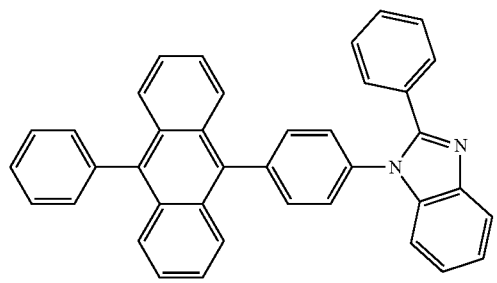
ET19
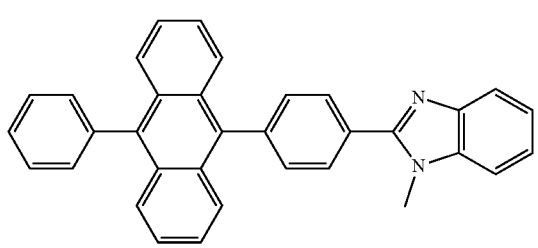

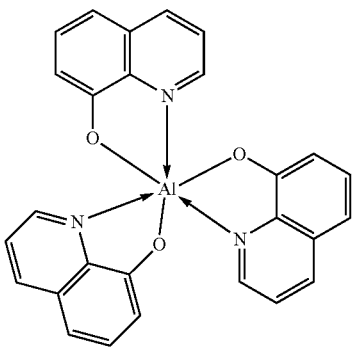

ET20

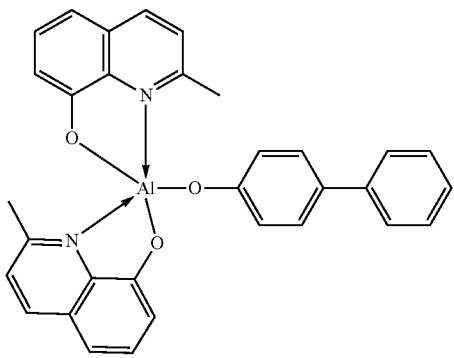

ET21

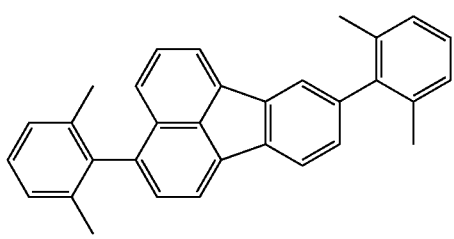

ET22

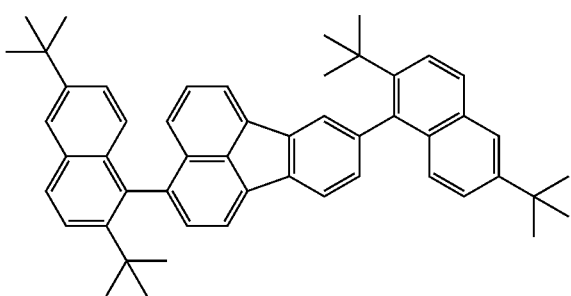

ET23

Configuration of Organic Light-Emitting Element

The organic light-emitting element is provided by forming an anode, an organic compound layer, and a cathode on a substrate. For example, a protective layer and a color filter may be disposed on the cathode. If the color filter is disposed, a planarizing layer may be disposed between the protective layer and the color filter. The planarizing layer may be formed of, for example, an acrylic resin.

Substrate

The substrate is formed of, for example, quartz, glass, silicon wafer, resin, or metal. A switching element such as a transistor and a wire may be disposed on the substrate, and an insulating layer may be disposed thereon. The insulating layer may be formed of any material as long as contact holes can be formed to establish electrical connection between the anode and the wire and the anode can be insulated from wires to which the anode is not connected. Examples of the material for the insulating layer include resins such as polyimide, silicon oxide, and silicon nitride.

Electrode

The electrode may be a pair of electrodes. The pair of electrodes may be an anode and a cathode. When an electric field is applied in a direction in which the organic light-emitting element emits light, the electrode having a high electric potential is an anode and the other electrode is a cathode. It can also be said that the electrode that supplies holes to the light-emitting layer is an anode and the electrode that supplies electrons is a cathode.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used.

These electrode materials may be used alone or in combination of two or more. The anode may have a single-layer structure or a multilayer structure.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the materials are not limited thereto. The electrode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver is preferably used and a silver alloy is more preferably used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The method for forming a cathode is not particularly limited. For example, a DC and AC sputtering method may be employed because good film coverage can be achieved to readily reduce the resistance.

Protective Layer

A protective layer may be disposed on the cathode. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into the organic compound layer. For example, after the formation of the cathode, the resulting substrate may be transferred to another chamber without breaking the vacuum, and a silicon nitride film having a thickness of 2 μm may be formed by a chemical vapor deposition (CVD) method to provide a protective layer. After the film formation by the CVD method, a protective layer may be disposed by an atomic layer deposition method (ALD method).

Color Filter

A color filter may be disposed on the protective layer. For example, a color filter provided in consideration of the size of organic light-emitting elements is disposed on another substrate, and this substrate may be bonded to the substrate on which the organic light-emitting elements have been disposed. Alternatively, a color filter may be patterned on the above-described protective layer by photolithography. The color filter may be formed of a polymer.

Planarizing Layer

A planarizing layer may be disposed between the color filter and the protective layer. The planarizing layer may be formed of an organic compound. The organic compound may be a low-molecular-weight organic compound or may be a high-molecular-weight organic compound, but is desirably a high-molecular-weight organic compound.

The planarizing layer may be disposed on and below the color filter, and both the planarizing layers may be formed of the same material or different materials. Specific examples of the material include polyvinyl carbazole resin, polycarbonate resin, polyester resin, ABS resin, acrylic resin, polyimide resin, phenolic resin, epoxy resin, silicone resin, and urea resin.

Counter Substrate

A counter substrate may be disposed on the planarizing layer. The name of the counter substrate is derived from the fact that the counter substrate is disposed at a position corresponding to that of the above-described substrate. The counter substrate may be formed of the same material as the above-described substrate.

Organic Compound Layer

The organic compound layers (e.g., a hole injection layer, a hole transport layer, an electron blocking layer, a light-emitting layer, a hole blocking layer, an electron transport layer, and an electron injection layer) that constitute the organic light-emitting element according to an embodiment of the present disclosure are formed by the following method.

The organic compound layers that constitute the organic light-emitting element according to an embodiment of the present disclosure can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed.

When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination.

Non-limiting examples of the binder resin include polyvinyl carbazole resin, polycarbonate resin, polyester resin, ABS resin, acrylic resin, polyimide resin, phenolic resin, epoxy resin, silicone resin, and urea resin.

These binder resins may be used alone as a homopolymer or in combination as a mixture of two or more as a copolymer. Furthermore, publicly known additives such as a plasticizer, an antioxidant, and an ultraviolet absorber may be optionally used in combination.

Application of Organic Light-Emitting Element According to Embodiment of the Present Disclosure The organic light-emitting element according to an embodiment of the present disclosure can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit. The display apparatus includes a plurality of pixels, and at least one of the plurality of pixels may include the organic light-emitting element according to this embodiment and a transistor connected to the organic light-emitting element.

The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

Figure 2:
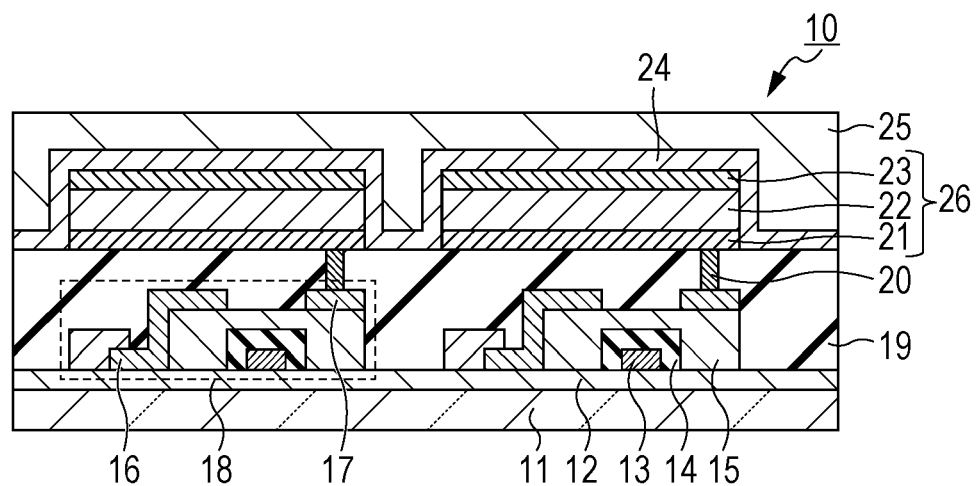
FIG. 2 is a schematic sectional view illustrating an example of a display apparatus including an organic light-emitting element according to an embodiment of the present disclosure.

Next, a display apparatus according to this embodiment will be described with reference to the attached drawings. FIG. 2 is a schematic sectional view illustrating an example of a display apparatus including organic light-emitting elements and TFT elements connected to the organic light-emitting elements. The TFT element is an example of active elements.

A display apparatus 10 in FIG. 2 includes a substrate 11 made of glass or the like and a moistureproof film 12 that is disposed on the substrate 11 and protects TFT elements or organic compound layers. The display apparatus 10 also includes metal gate electrodes 13, gate insulating films 14, and semiconductor layers 15.

Each of the TFT elements 18 includes a semiconductor layer 15, a drain electrode 16, and a source electrode 17. An insulating film 19 is disposed on the TFT element 18. An anode 21 that constitutes an organic light-emitting element 26 and the source electrode 17 are connected to each other through a contact hole 20.

The form of electrical connection between electrodes (anode 21 and cathode 23) included in the organic light-emitting element 26 and electrodes (source electrode 17 and drain electrode 16) included in the TFT element 18 is not limited to the form illustrated in FIG. 2. That is, it suffices that one of the anode 21 and the cathode 23 is electrically connected to one of the source electrode 17 and the drain electrode 16 of the TFT element 18.

In the display apparatus 10 in FIG. 2, an organic compound layer 22 is illustrated as if having a single-layer structure, but may have a multilayer structure. A first protective layer 24 and a second protective layer 25 for suppressing the deterioration of the organic light-emitting element 26 are disposed on the cathode 23.

In the display apparatus 10 in FIG. 2, a transistor is used as a switching element. Instead, an MIM element may be used as a switching element.

The transistor used in the display apparatus 10 in FIG. 2 is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements.

The transistor included in the display apparatus 10 in FIG. 2 may be formed in a substrate such as a Si substrate. Herein, the phrase "formed in a substrate" means that a transistor is produced by processing the substrate itself, such as a Si substrate. That is, a transistor formed in a substrate can be regarded as a transistor integrally formed with a substrate.

In the organic light-emitting element according to this embodiment, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "in a substrate". The size of a display unit determines whether a transistor is disposed in a substrate or a TFT is used. For example, in the case of a size of about 0.5 inches, the organic light-emitting element may be disposed on a Si substrate.

Figure 3:
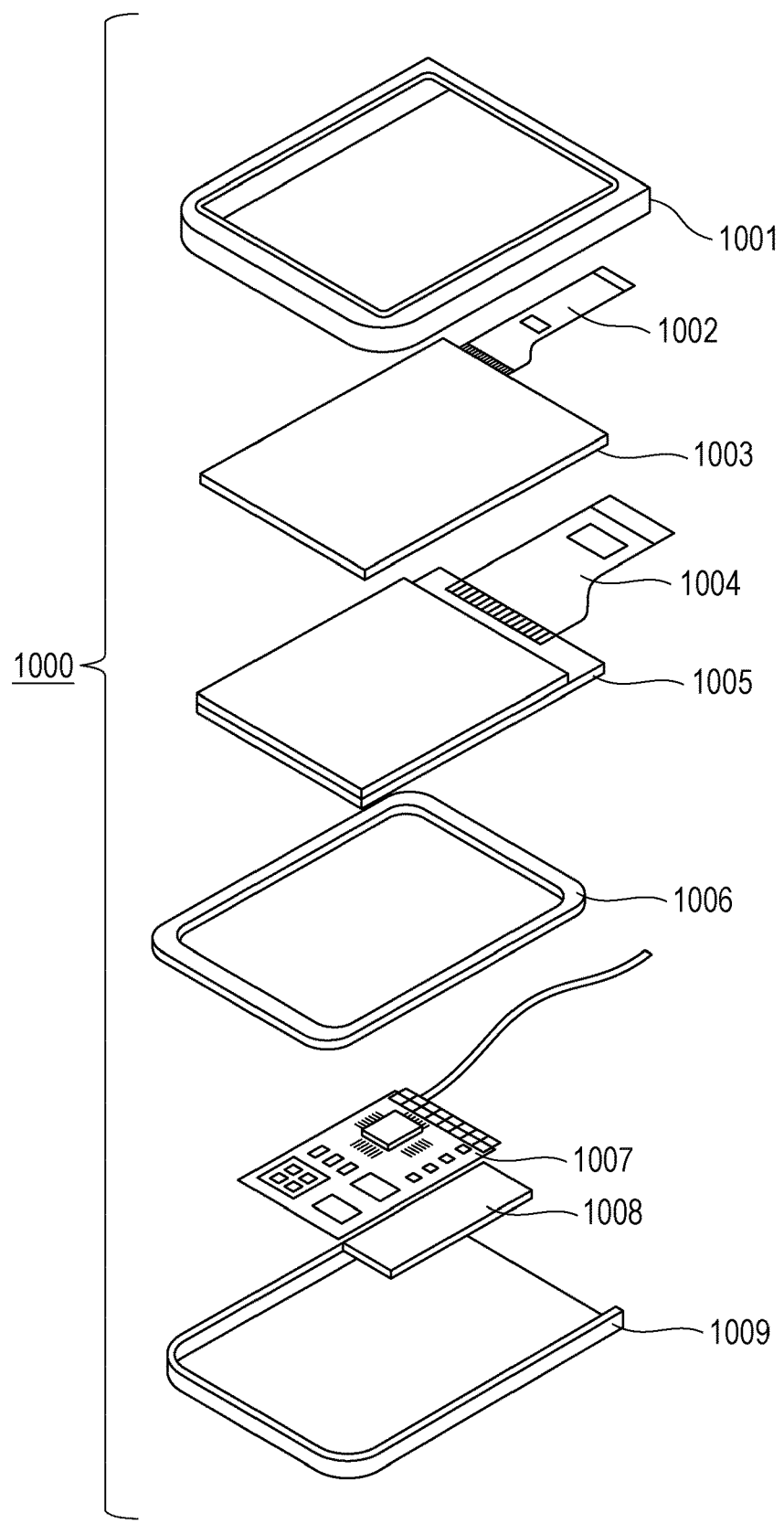
FIG. 3 schematically illustrates an example of a display apparatus according to an embodiment of the present disclosure.

FIG. 3 schematically illustrates an example of a display apparatus according to this embodiment. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. A transistor is printed on the circuit board 1007. The battery 1008 is not necessarily disposed if the display apparatus is not a mobile apparatus. Even if the display apparatus is a mobile apparatus, the battery 1008 may be disposed at a different position.

The display apparatus according to this embodiment may be used in a display unit of a photoelectric conversion apparatus such as an image pickup apparatus that includes an optical unit including a plurality of lenses and an image pickup element configured to receive light that has passed through the optical unit. The image pickup apparatus may include a display unit configured to display information obtained by the image pickup element. The display unit may be a display unit exposed to the outside of the image pickup apparatus or a display unit disposed in a viewfinder. The image pickup apparatus may be a digital camera or a digital camcorder.

Figure 4A:
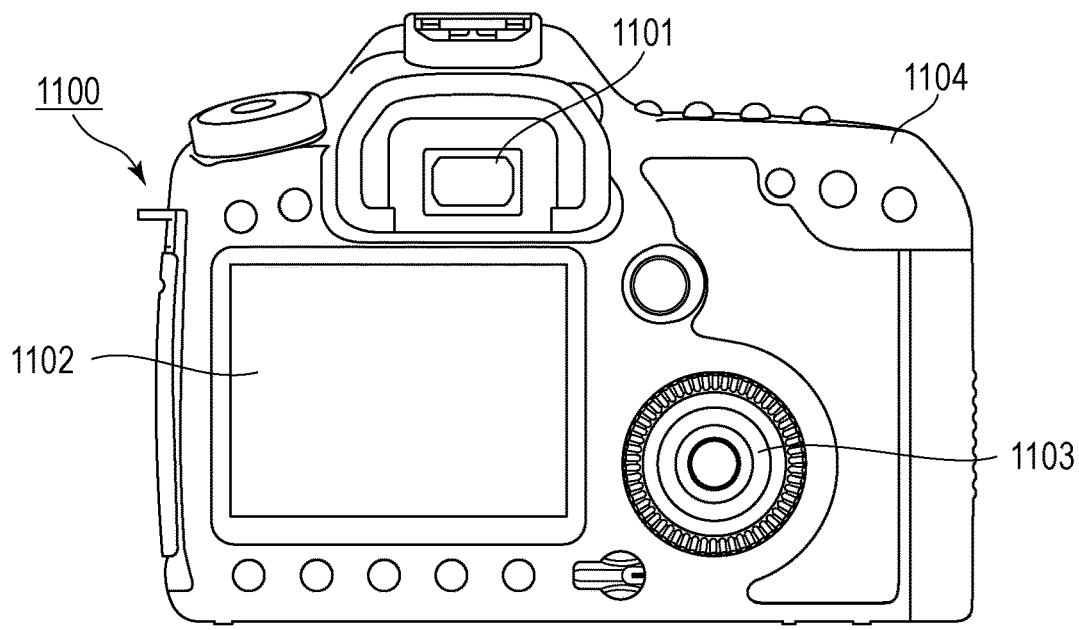
FIG. 4A schematically illustrates an example of an image pickup apparatus according to an embodiment of the present disclosure.

FIG. 4A schematically illustrates an example of an image pickup apparatus according to this embodiment. An image pickup apparatus 1100 may include a viewfinder 1101, a rear display 1102, an operating unit 1103, and a housing 1104. The viewfinder 1101 may include the display apparatus according to this embodiment. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Therefore, the display apparatus including the organic light-emitting element according to this embodiment may be used. This is because the organic light-emitting element has a high response speed. The display apparatus including the organic light-emitting element can be more suitably used than these apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

The display apparatus according to this embodiment may include red, green, and blue color filters. The red, green, and blue color filters may be disposed in a delta arrangement.

The display apparatus according to this embodiment may be used in a display unit of an electronic apparatus such as a mobile terminal. The display unit may have both a display function and an operational function. Examples of the mobile terminal include cellular phones such as smartphones, tablet computers, and head-mounted displays.

Figure 4B:
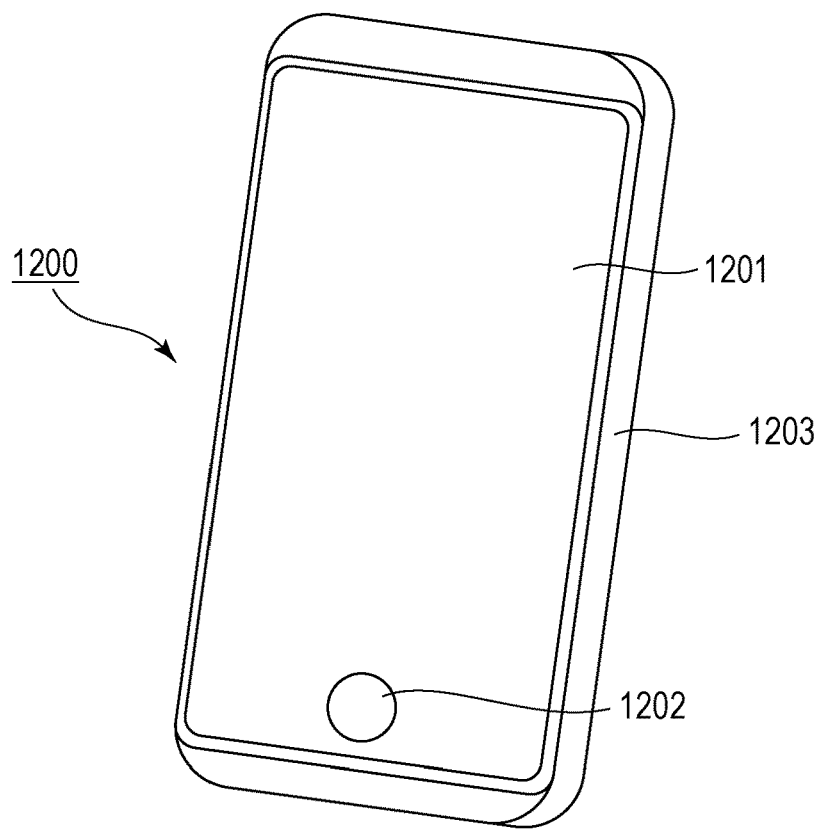
FIG. 4B schematically illustrates an example of an electronic apparatus according to an embodiment of the present disclosure.

FIG. 4B schematically illustrates an example of an electronic apparatus according to this embodiment. An electronic apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. An electronic apparatus including a communication unit may be referred to as a communication apparatus.

Figure 5A:
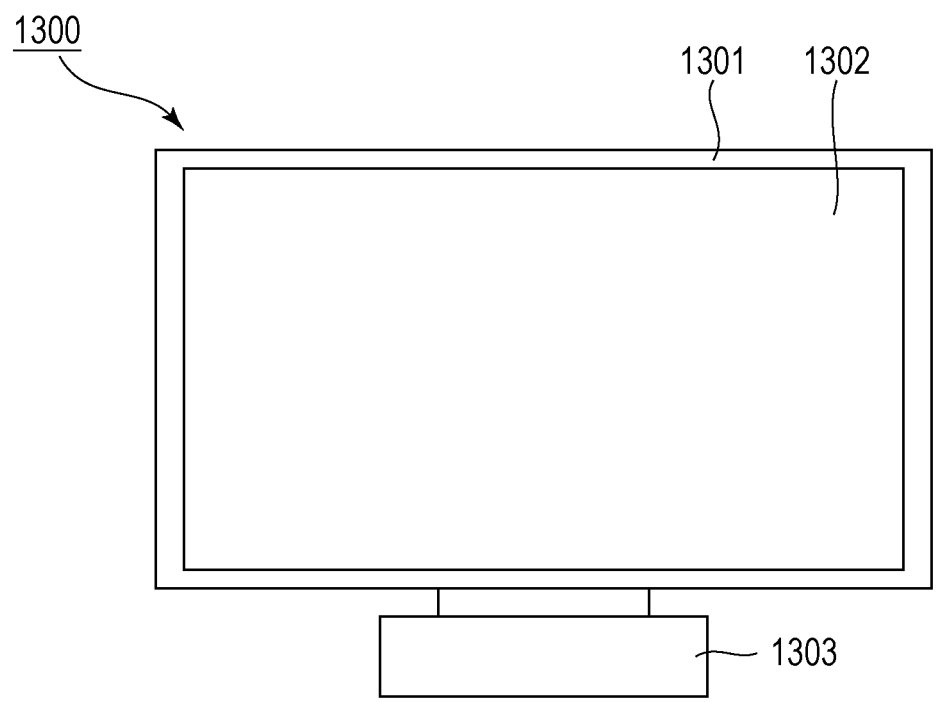
FIG. 5A schematically illustrates an example of a display apparatus according to an embodiment of the present disclosure.
Figure 5B:
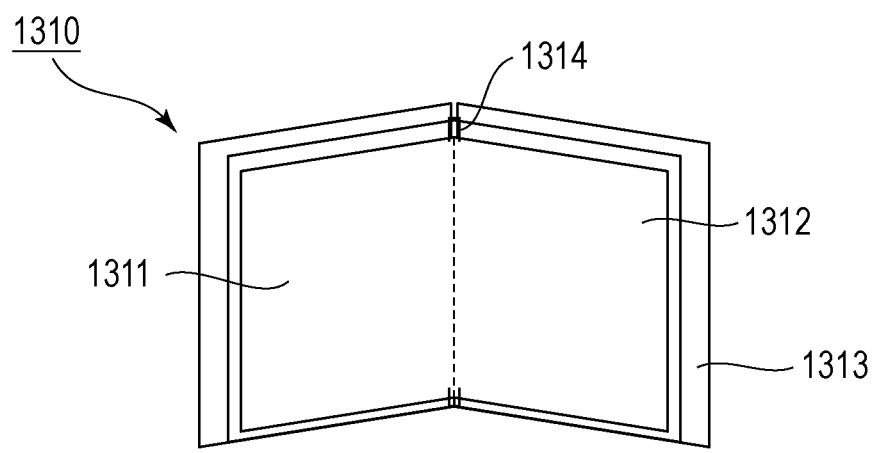
FIG. 5B schematically illustrates an example of a foldable display apparatus.

FIGS. 5A and 5B schematically illustrate examples of display apparatuses according to this embodiment. FIG. 5A illustrates a display apparatus such as a television monitor or a PC monitor. A display apparatus 1300 includes a frame 1301 and a display unit 1302. A light-emitting device according to this embodiment may be used for the display unit 1302. The display apparatus 1300 includes the frame 1301 and a base 1303 that supports the display unit 1302. The form of the base 1303 is not limited to that in FIG. 5A. The lower side of the frame 1301 may also serve as a base. The frame 1301 and the display unit 1302 may be curved. The radius of curvature may be 5000 mm or more and 6000 mm or less.

FIG. 5B schematically illustrates another example of the display apparatus according to this embodiment. A display apparatus 1310 in FIG. 5B is a so-called foldable display apparatus. The display apparatus 1310 includes a first display unit 1311, a second display unit 1312, a housing 1313, and a bending point 1314. The first display unit 1311 and the second display unit 1312 may include the light-emitting device according to this embodiment. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Figure 6A:
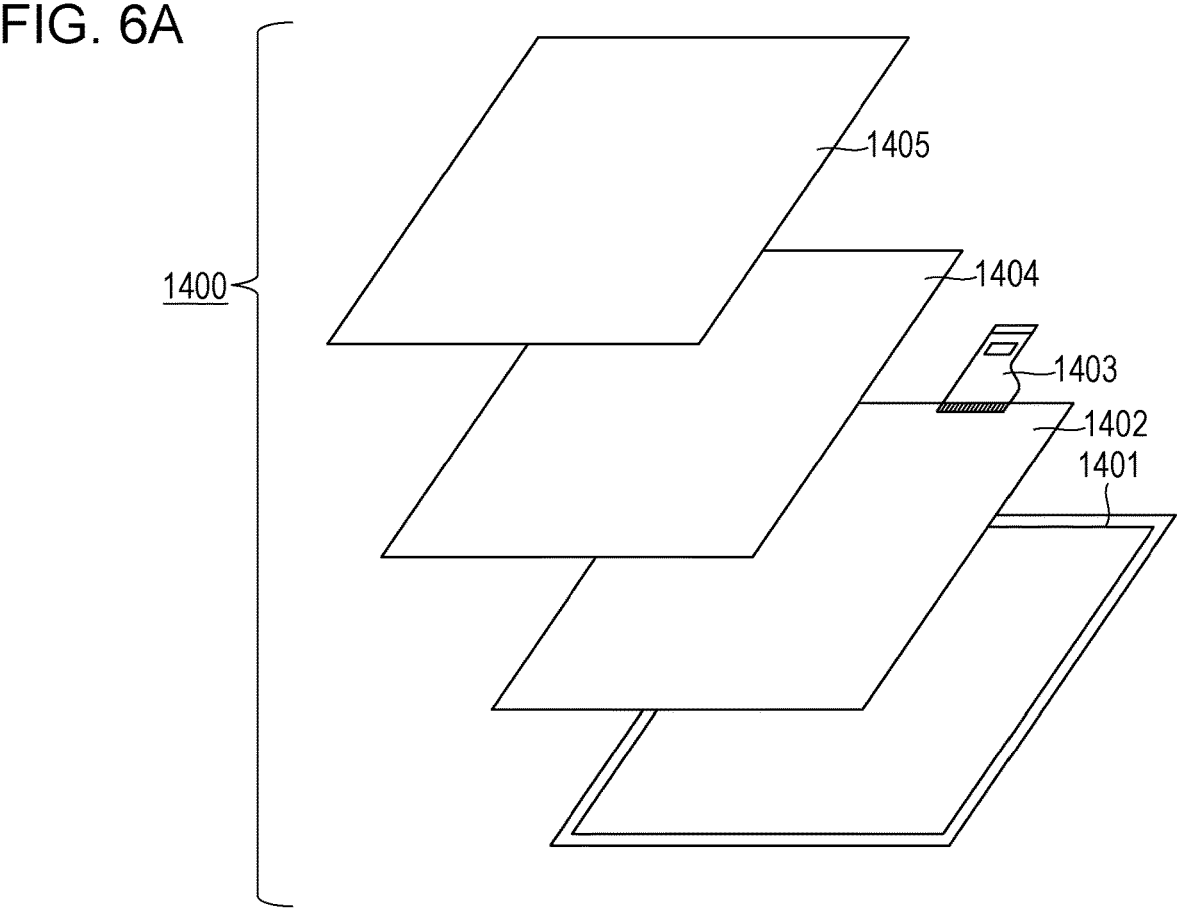
FIG. 6A schematically illustrates an example of a lighting apparatus according to an embodiment of the present disclosure.

FIG. 6A schematically illustrates an example of a lighting apparatus according to this embodiment. A lighting apparatus 1400 may include a housing 1401, a light source 1402, a circuit board 1403, and an optical filter 1404 and a light diffusion unit 1405 that transmit light emitted from the light source 1402. The light source 1402 may include the organic light-emitting element according to this embodiment. The optical filter 1404 may be a filter for improving the color rendering of the light source. The light diffusion unit 1405 used for lighting up or the like effectively diffuses light from the light source and allows the light to reach a wide area. The optical filter 1404 and the light diffusion unit 1405 may be disposed on the light-emitting side of the lighting apparatus. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to this embodiment and a power supply circuit connected to the organic light-emitting element. The power supply circuit is a circuit that converts an alternating voltage to a direct voltage. The color "white" has a color temperature of 4200 K and the color "natural white" has a color temperature of 5000 K. The lighting apparatus may include a color filter.

The lighting apparatus according to this embodiment may include a heat dissipation unit. The heat dissipation unit dissipates heat in the apparatus to the outside and is formed of, for example, a metal having a high specific heat or a liquid silicon.

Figure 6B:
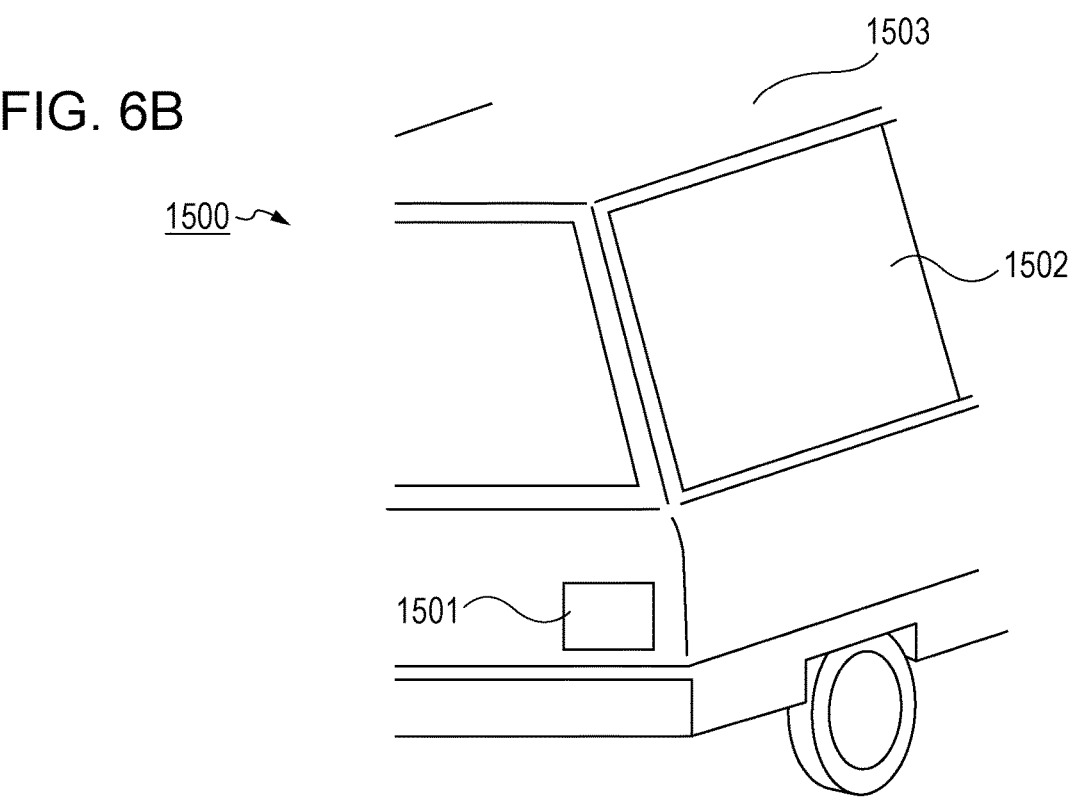
FIG. 6B schematically illustrates an example of an automobile including a lighting fixture for vehicles according to an embodiment of the present disclosure.

FIG. 6B schematically illustrates an automobile that is an example of a moving object according to this embodiment. The automobile includes a tail lamp that is an example of a lighting fixture. An automobile 1500 includes a tail lamp 1501, and the tail lamp may be lit through, for example, application of the brake.

The tail lamp 1501 may include the organic light-emitting element according to this embodiment. The tail lamp 1501 may include a protective member that protects the organic light-emitting element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative.

The automobile 1500 may include a car body 1503 and windows 1502 attached to the car body 1503. The windows 1502 may be transparent displays as long as the windows 1502 are not a front or rear window of the automobile. The transparent display may include the organic light-emitting element according to this embodiment. In this case, members, such as an electrode, included in the organic light-emitting element are formed of a transparent material.

The moving object according to this embodiment may be, for example, a ship, an aircraft, or a drone. The moving object may include a body and a lighting fixture disposed on the body. The lighting fixture may emit light for allowing the position of the body to be recognized. The lighting fixture may include the organic light-emitting element according to this embodiment.

As described above, use of an apparatus including the organic light-emitting element according to this embodiment allows stable display with a good image quality for a long time.

EXAMPLES

Hereafter, the present disclosure will be described based on Examples. However, the present disclosure is not limited thereto.

Example 1 (Synthesis of Exemplary Compound A1)

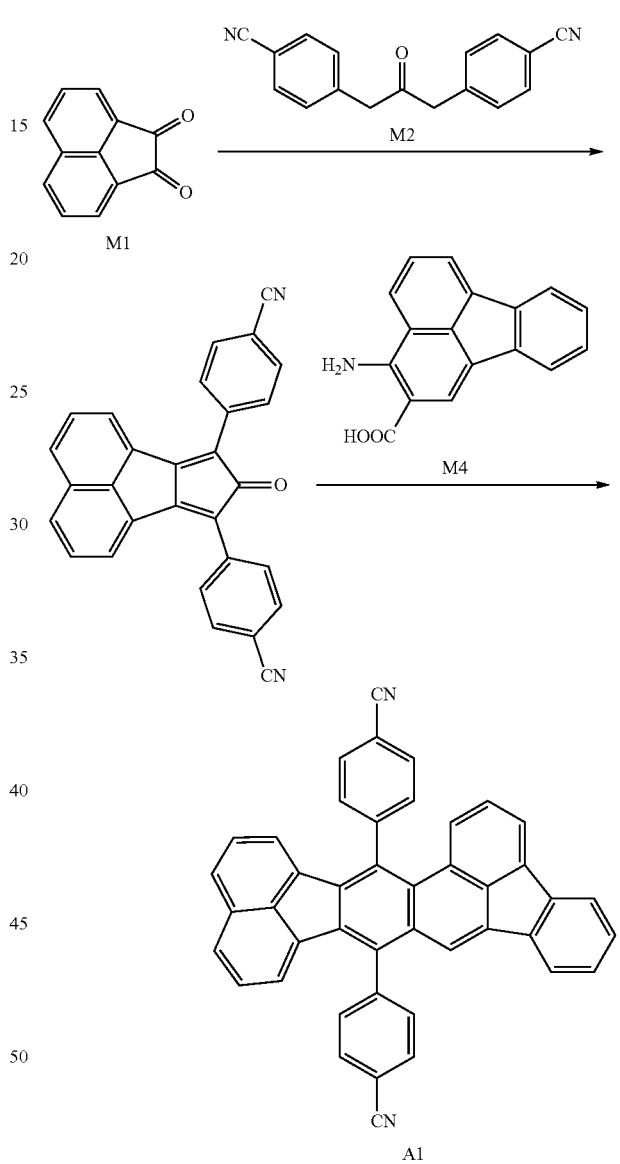

(1) Synthesis of Compound M3

The following reagents and solvent were charged into a 200 ml recovery flask.
Compound M1: 3.64 g (20 mmol)
Compound M2: 5.21 g (20 mmol)
Ethanol: 150 mL Subsequently, the reaction solution was heated to 70° C. in a nitrogen stream, and a KOH ethanol solution was added dropwise thereto. Furthermore, stirring was performed at this temperature (70° C.) for 5 hours. After the completion of the reaction, water was added and the resulting precipitate was separated. The separated product was washed by dispersion with methanol to obtain 5.69 g of a dark gray compound M3 (yield: 70%).

(2) Synthesis of Exemplary Compound A1

The following reagents and solvent were charged into a 200 ml recovery flask.
Compound M3: 4.06 g (10 mmol)
Compound M4: 3.14 g (12 mmol)
Isoamyl nitrite: 2.00 mL (15 mmol)
Toluene: 100 mL
Subsequently, the reaction solution was heated to 105° C. in a nitrogen stream, and stirring was performed at this temperature (105° C.) for 4 hours. After the completion of the reaction, extraction was performed using toluene and water. The resulting product was concentrated, purified by silica gel column chromatography (heptane:toluene=1:1), and then washed by dispersion with heptane/ethanol to obtain 4.34 g of a yellow compound A1 (yield: 75%). This compound was confirmed to have a purity of 99% or more, as measured by HPLC.

The emission spectrum of a toluene solution of the exemplary compound A1 at $1 \times 10^{-5}$ mol/L was determined by photoluminescence measurement at an excitation wavelength of 350 nm using an F-4500 manufactured by Hitachi, Ltd. As a result, a spectrum having the maximum intensity at 438 nm was obtained.

The exemplary compound A1 was subjected to mass spectrometry using MALDI-TOF-MS (Autoflex LRF manufactured by Bruker).
MALDI-TOF-MS
Measured value: m/z=579, Calculated value: $C_{44}H_{22}N_2=578$ Examples 2 to 6 (Synthesis of Exemplary Compounds)

Exemplary compounds listed in Tables 4 and 5 were synthesized in the same manner as in Example 1, except that the raw materials M1 and M2 in Example 1 were changed to the raw materials 1 and 2, respectively. The measured value m/z of mass spectrometry performed in the same manner as in Example 1 is also shown.

TABLE 4

| Example | Exemplary compound | Raw material 1 | Raw material 2 | m/z |
|---|---|---|---|---|
| 2 | 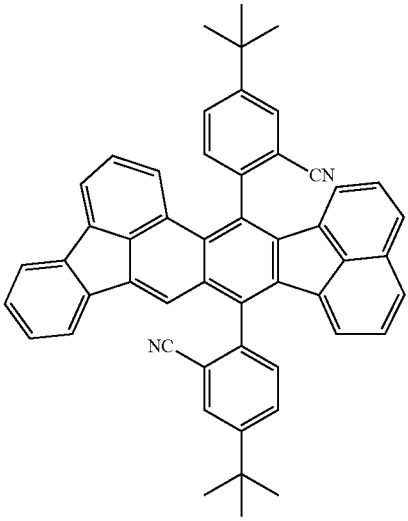<br>A5 | M1 | 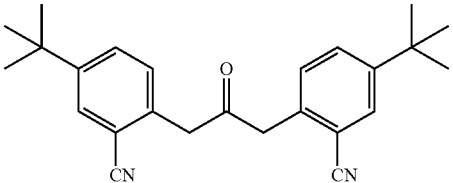 [SMILES: CC(C)(C)c1ccc(CC(=O)Cc2ccc(C(C)(C)C)cc2C#N)c(C#N)c1] | 690 |
| 3 | 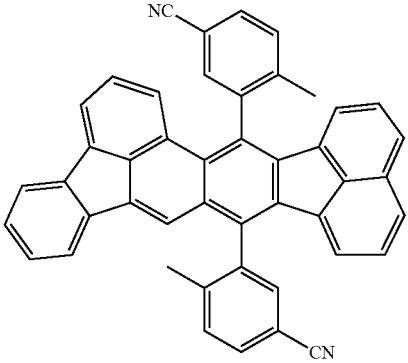<br>B3 | M1 | 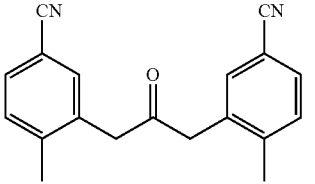 [SMILES: Cc1ccc(C#N)cc1CC(=O)Cc1cc(C#N)ccc1C] | 607 |

TABLE 4-continued
| Example | Exemplary compound | Raw material 1 | Raw material 2 | m/z |
|---|---|---|---|---|
| 4 | 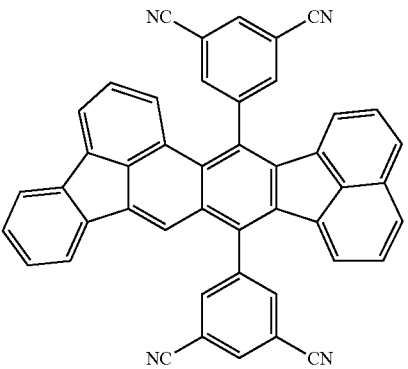<br>C1 | M1 | 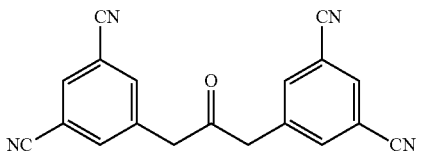 [SMILES: N#Cc1cc(C#N)cc(CC(=O)Cc2cc(C#N)cc(C#N)c2)c1] | 629 |
TABLE 5
| Example | Exemplary compound | Raw material 1 | Raw material 2 | m/z |
|---|---|---|---|---|
| 5 | 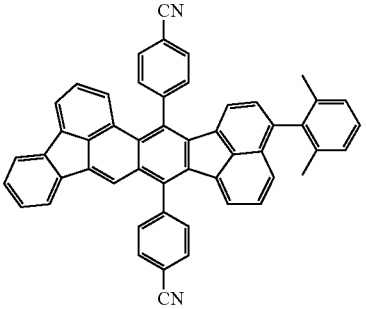<br>A7<br>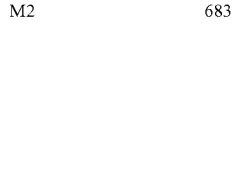<br>A8 | 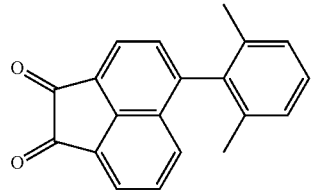 [SMILES: Cc1cccc(C)c1-c1ccc2c3c(cccc13)C(=O)C2=O] | M2 | 683 |
| 6 | 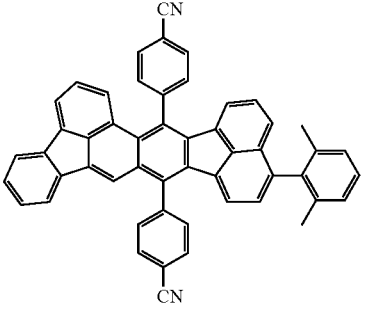<br>B7 | 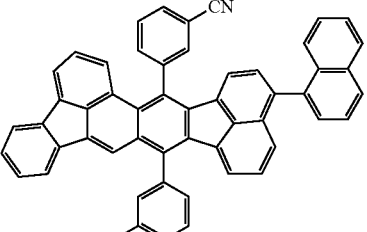 | 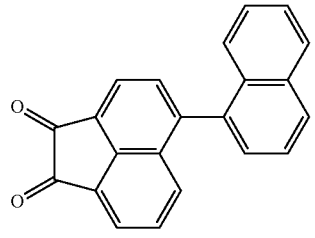 | 755 |

TABLE 5-continued

| Example | Exemplary compound | Raw material 1 | Raw material 2 | m/z |
|---|---|---|---|---|
| | 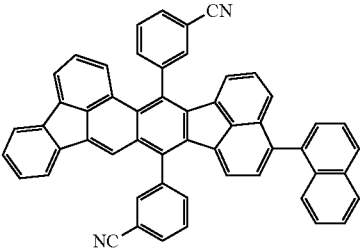 B8 | | | |

Example 7

In this Example, a bottom-emission organic EL element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process. Subsequently, the organic EL layers and the electrode layer shown in Table 6 were successively formed on the ITO substrate by performing vacuum vapor deposition through resistance heating in a vacuum chamber at $1.33 \times 10^{-4}$ Pa. At this time, the electrode area of a counter electrode (metal electrode layer, cathode) was set to 3 mm$^2$.

TABLE 6

| | Material | Thickness (nm) |
|---|---|---|
| Anode | Al | 100 |
| Electron injection layer (EIL) | LiF | 1 |
| Electron transport layer (ETL) | ET2 | 20 |
| Hole blocking layer (HBL) | ET12 | 20 |
| Light-emitting layer (EML) | Host EM4  Guest A3 | Weight ratio EM4:B3 = 99.3:0.7 | 30 |
| Electron blocking layer (EBL) | HT12 | 15 |
| Hole transport layer (HTL) | HT3 | 30 |
| Hole injection layer (HIL) | HT16 | 5 |

The characteristics of the obtained element were measured and evaluated. The light-emitting element had a maximum emission wavelength of 449 nm and a maximum external quantum efficiency (E.Q.E) of 5.8%, and emitted blue light with a chromaticity of (X, Y)=(0.14, 0.08). For the measurement instrument, specifically, the current-voltage characteristics were measured with a microammeter 4140B manufactured by Hewlett-Packard Company, and the emission luminance was measured with a BM7 manufactured by TOPCON Corporation. Furthermore, a continuous driving test at a current density of 100 mA/cm$^2$ was performed to measure a time (LT90) taken when the luminance decrease reached 10%. The time was more than 100 hours. Table 7 shows the measurement results. Examples 8 to 13 and Comparative Examples 1 and 2

Organic light-emitting elements were produced by the same method as in Example 7, except that the compounds were appropriately changed to those listed in Table 7. The characteristics of the obtained elements were measured and evaluated in the same manner as in Example 7. Table 7 shows the measurement results.

TABLE 7

| | | | | EML | | | | E.Q.E [%] | LT90 [h] | Blue chromaticity coordinates (x, y) |
|---|---|---|---|---|---|---|---|---|---|---|
| | HIL | HTL | EBL | Host | Guest | HBL | ETL | | | |
| Example 7 | HT16 | HT3 | HT12 | EM4 | A3 | ET12 | ET2 | 5.8 | 120 | (0.14, 0.08) |
| Example 8 | HT16 | HT2 | HT11 | EM3 | A4 | ET12 | ET2 | 5.4 | 130 | (0.14, 0.10) |
| Example 9 | HT16 | HT2 | HT12 | EM4 | A7 | ET12 | ET2 | 5.6 | 115 | (0.14, 0.09) |
| Example 10 | HT16 | HT3 | HT11 | EM3 | B1 | ET10 | ET2 | 5.8 | 105 | (0.14, 0.07) |
| Example 11 | HT16 | HT2 | HT8 | EM6 | B7, B8 | ET12 | ET3 | 6.2 | 110 | (0.14, 0.09) |
| Example 12 | HT2 | HT2 | HT8 | EM3 | C1 | ET18 | ET3 | 6.0 | 115 | (0.14, 0.10) |

TABLE 7-continued

| | | | | EML | | | | E.Q.E [%] | LT90 [h] | Blue chromaticity coordinates (x, y) |
|---|---|---|---|---|---|---|---|---|---|---|
| | HIL | HTL | EBL | Host | Guest | HBL | ETL | | | |
| Example 13 | HT16 | HT2 | HT12 | EM4 | C5, C6 | ET12 | ET2 | 5.7 | 120 | (0.14, 0.12) |
| Comparative Example 1 | HT16 | HT3 | HT12 | EM13 | Comparative compound 1-B | ET12 | ET2 | 5.2 | 100 | (0.14, 0.15) |
| Comparative Example 2 | HT16 | HT3 | HT12 | EM4 | Comparative compound 1-C | ET10 | ET2 | 5.5 | 90 | (0.14, 0.17) |

Table 7 shows that the chromaticity coordinates in Comparative Examples 1 and 2 were (0.14, 0.15) and (0.14, 0.17), respectively, and the light-emitting elements in Comparative Examples 1 and 2 emitted blue light with a lower color purity than blue light-emitting elements including the compound according to the present disclosure in a blue light-emitting layer. In contrast, the elements including the organic compound according to the present disclosure had good blue light-emitting properties and high durability.

Example 14

In this Example, a top-emission organic EL element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film having a thickness of 40 nm was formed on a glass substrate by a sputtering method and patterned by photolithography to form an anode. At this time, the electrode area of a counter electrode (metal electrode layer, cathode) was set to 3 mm². Subsequently, the cleaned substrate on which the electrode had been formed and materials were placed in a vacuum evaporation system (manufactured by ULVAC, Inc.), and the system was evacuated to a pressure of $1.33 \times 10^{-4}$ Pa ($1 \times 10^{-6}$ Torr) and then UV/ozone cleaning was performed. Subsequently, layers shown in Table 8 were formed. Lastly, sealing was performed in a nitrogen atmosphere.

TABLE 8

| | Material | | | Thickness (nm) |
|---|---|---|---|---|
| Anode | Mg Ag | | Weight ratio Mg:Ag = 50:50 | 10 |
| Electron injection layer (EIL) | LiF | | | 1 |
| Electron transport layer (ETL) | ET2 | | | 30 |
| Hole blocking layer (HBL) | ET12 | | | 70 |
| Second light-emitting layer (2nd EML) | Second host Second guest (blue dopant) | EM1 B3 | Weight ratio EM1:B8 = 99.2:0.8 | 10 |
| First light-emitting layer (1st EML) | First host First guest (red dopant) Third guest (green dopant) | EM1 RD1 GD8 | Weight ratio EM1:RD1:GD8 = 96.7:0.3:3.0 | 10 |

TABLE 8-continued

| | Material | Thickness (nm) |
|---|---|---|
| Electron blocking layer (EBL) | HT7 | 10 |
| Hole transport layer (HTL) | HT2 | 20 |
| Hole injection layer (HIL) | HT16 | 5 |

The characteristics of the obtained element were measured and evaluated. The obtained element exhibited good white light emission. Furthermore, a continuous driving test at an initial luminance of 2000 cd/m² was performed to measure a luminance decrease after 100 hours. Table 9 shows the results.

Examples 15 to 18 and Comparative Examples 3 and 4

Organic light-emitting elements were produced by the same method as in Example 14, except that the compounds were appropriately changed to those listed in Table 9. The characteristics of the obtained elements were measured and evaluated in the same manner as in Example 14. Table 9 shows the measurement results.

TABLE 9

| | 1st EML | | | 2nd EML | | Luminance decrease [%] |
|---|---|---|---|---|---|---|
| | First host | First guest | Third guest | Second host | Second guest | |
| Example 14 | EM1 | RD1 | GD8 | EM1 | B3 | 12 |
| Example 15 | EM1 | RD1 | GD8 | EM3 | A1 | 10 |
| Example 16 | EM1 | RD1 | GD5 | EM1 | C1 | 10 |
| Example 17 | EM5 | RD1 | GD6 | EM5 | B5, B6 | 12 |
| Example 18 | EM11 | RD2 | GD5 | EM11 | A11, A12 | 12 |
| Comparative Example 3 | EM1 | RD1 | GD5 | EM1 | Comparative compound 1-D | 20 |
| Comparative Example 4 | EM1 | RD1 | GD8 | EM1 | Comparative compound 1-E | 25 |

Table 9 shows that the organic light-emitting elements including the comparative compounds 1-D and 1-E had luminance decreases of 20% and 25%, respectively. This is because when the comparative compound is used as a guest, the reduction potential is low and the electron acceptability is not sufficient and therefore the organic light-emitting elements have poor chemical stability.

The organic compound according to the present disclosure is a blue light-emitting material having a high reduction potential, high electron acceptability, and a high color purity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-202381, filed Nov. 7, 2019, which is hereby incorporated by reference herein in its entirety.

What is claimed is:

1. An organic compound represented by formula [1],

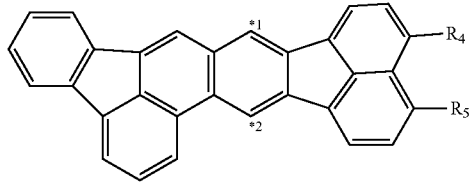

[1]

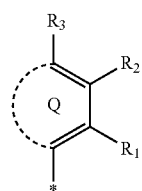

[1-1]

wherein rings Q represented by formula [1-1] are each independently present at positions *1 and *2 such that positions * of the rings Q correspond to the positions *1 and *2, the rings Q may be the same or different, $R_4$ and $R_5$ represent groups each independently selected from the group consisting of a hydrogen atom and a substituted or unsubstituted aryl group, the rings Q are aromatic hydrocarbons, $R_1$ to $R_3$ represent groups each independently selected from the group consisting of a hydrogen atom, a substituted or unsubstituted alkyl group, a substituted or unsubstituted aryl group, and a cyano group, and at least one of $R_1$ to $R_3$ represents a cyano group.

2. The organic compound according to claim 1, wherein the organic compound is represented by formula [2],

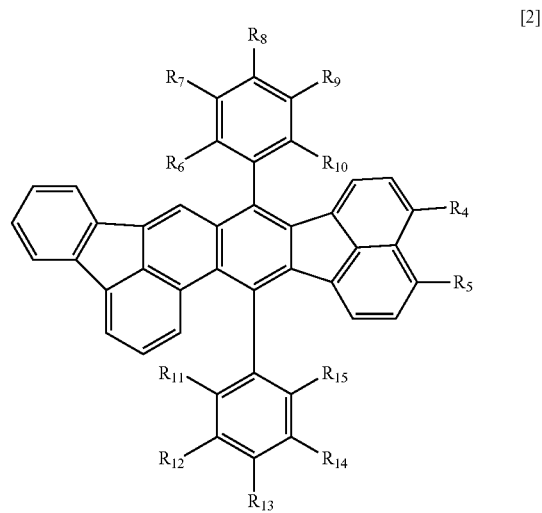

[2]

wherein $R_6$ to $R_{15}$ represent groups each independently selected from the group consisting of a hydrogen atom, a substituted or unsubstituted alkyl group, a substituted or unsubstituted aryl group, and a cyano group, and at least one of $R_6$ to $R_{15}$ represents a cyano group.

3. The organic compound according to claim 2, wherein at least two of $R_7$ to $R_9$ represent a cyano group, and at least two of $R_{12}$ to $R_{10}$ represent a cyano group.

4. The organic compound according to claim 2, wherein $R_7$ or $R_9$ represents a cyano group, and $R_{12}$ or $R_{14}$ represents a cyano group.

5. The organic compound according to claim 2, wherein any one of $R_6$ to $R_{10}$ represents a cyano group, and wherein any one of $R_{11}$ to $R_{15}$ represents a cyano group.

6. The organic compound according to claim 2, wherein $R_8$ and $R_{13}$ represent a cyano group.

7. The organic compound according to claim 1, wherein at least one of $R_4$ and $R_5$ represents a hydrogen atom.

8. The organic compound according to claim 1, wherein one of $R_4$ and $R_5$ represents a hydrogen atom and the other represents a group selected from the group consisting of a substituted or unsubstituted phenyl group, a substituted or unsubstituted naphthyl group, a substituted or unsubstituted fluorenyl group, and a substituted or unsubstituted phenanthrenyl group.

9. The organic compound according to claim 1, wherein $R_4$ and $R_5$ represent a group having no lone pair.

10. The organic compound according to claim 1, wherein any one of $R_1$ to $R_3$ represents a cyano group.

11. The organic compound according to claim 1, wherein $R_2$ or $R_3$ represents a cyano group.

12. An organic light-emitting element comprising:
an anode;
a cathode; and
an organic compound layer disposed between the anode and the cathode,
wherein at least one layer in the organic compound layer includes the organic compound according to claim 1.

13. The organic light-emitting element according to claim 12, wherein the layer including the organic compound is a light-emitting layer.

14. The organic light-emitting element according to claim 13,
wherein the organic compound layer further includes another light-emitting layer disposed together with the light-emitting layer so as to form a multilayer structure, and
the other light-emitting layer emits light having a color different from a color of light emitted from the light-emitting layer.

15. The organic light-emitting element according to claim 14, wherein the organic light-emitting element emits white light.

16. A display apparatus comprising a plurality of pixels, wherein at least one of the plurality of pixels includes the organic light-emitting element according to claim 12 and a transistor connected to the organic light-emitting element.

17. A photoelectric conversion apparatus comprising:
an optical unit including a plurality of lenses;
an image pickup element that receives light which has passed through the optical unit; and
a display unit that displays an image captured by the image pickup element,
wherein the display unit includes the organic light-emitting element according to claim 8.

18. An electronic apparatus comprising:
a display unit including the organic light-emitting element according to claim 12;
a housing in which the display unit is disposed; and
a communication unit that is disposed in the housing and communicates with an external unit.

19. A lighting apparatus comprising:
a light source including the organic light-emitting element according to claim 12; and
a light diffusion unit or an optical filter that transmits light emitted from the light source.

20. A moving object comprising:
a lighting fixture including the organic light-emitting element according to claim 12; and
a body on which the lighting fixture is disposed.

* * * * *